(12) United States Patent
Lauer

(10) Patent No.: US 8,721,883 B2
(45) Date of Patent: May 13, 2014

(54) MEDICAL FLUID CASSETTES AND RELATED SYSTEMS

(75) Inventor: Martin Lauer, St. Wendel (DE)

(73) Assignee: Fresenius Medical Care Deutschland GmbH, Bad Homburg (DE)

(*) Notice: Subject to any disclaimer, the term of this patent is extended or adjusted under 35 U.S.C. 154(b) by 0 days.

(21) Appl. No.: 13/401,419

(22) Filed: Feb. 21, 2012

(65) Prior Publication Data

US 2012/0181226 A1   Jul. 19, 2012

Related U.S. Application Data

(63) Continuation of application No. 12/627,043, filed on Nov. 30, 2009, now Pat. No. 8,142,653, which is a continuation of application No. 10/516,528, filed as application No. PCT/EP03/05377 on May 22, 2003, now Pat. No. 7,648,627.

(30) Foreign Application Priority Data

Jun. 4, 2002 (DE) .................. 102 24 750

(51) Int. Cl.
*A61M 1/16* (2006.01)
*A61M 1/36* (2006.01)

(52) U.S. Cl.
CPC ............... *A61M 1/16* (2013.01); *A61M 1/3621* (2013.01); *A61M 2205/128* (2013.01)
USPC ......... 210/240; 210/321.6; 604/5.04; 604/6.1

(58) Field of Classification Search
None
See application file for complete search history.

(56) References Cited

U.S. PATENT DOCUMENTS

| | | | |
|---|---|---|---|
| 329,773 | A | 11/1885 | Perry |
| 2,383,193 | A | 8/1945 | Herbert |
| 2,711,134 | A | 6/1955 | Hughes |
| 2,886,281 | A | 5/1959 | Canalizo |
| 3,083,943 | A | 4/1963 | Stewart, Jr. et al. |
| 3,323,786 | A | 6/1967 | Boschi |
| 3,556,465 | A | 1/1971 | Little |
| 3,689,025 | A | 9/1972 | Kiser et al. |
| 3,927,955 | A | 12/1975 | Spinosa et al. |
| 3,966,358 | A | 6/1976 | Heimes et al. |
| 3,985,135 | A | 10/1976 | Carpenter et al. |
| 4,026,669 | A | 5/1977 | Leonard et al. |
| 4,152,098 | A | 5/1979 | Moody et al. |
| 4,178,940 | A | 12/1979 | Au |

(Continued)

FOREIGN PATENT DOCUMENTS

| | | |
|---|---|---|
| CA | 2101232 A | 1/1983 |
| DE | 2628238 | 1/1978 |

(Continued)

OTHER PUBLICATIONS

Gambro®, "DEHP-free cartridge blood sets," © Nov. 2004, Gambro, Inc., Lakewood, CO, 4 pp.

(Continued)

*Primary Examiner* — Terry Cecil
(74) *Attorney, Agent, or Firm* — Fish & Richardson P.C.

(57) ABSTRACT

The invention relates to an apparatus for the treatment of a medical liquid comprising a liquid treatment machine and a cassette insertable therein substantially made of a rigid base body of the cassette with fitted chambers and passages and a foil covering them.

37 Claims, 15 Drawing Sheets

(56) References Cited

U.S. PATENT DOCUMENTS

| | | |
|---|---|---|
| 4,273,121 A | 6/1981 | Jassawalla |
| 4,303,376 A | 12/1981 | Siekmann |
| 4,322,201 A | 3/1982 | Archibald |
| 4,333,452 A | 6/1982 | Au |
| 4,370,983 A | 2/1983 | Lichtenstein |
| 4,382,753 A | 5/1983 | Archibald |
| 4,410,322 A | 10/1983 | Archibald |
| 4,412,553 A | 11/1983 | Kopp et al. |
| 4,436,620 A | 3/1984 | Bellotti et al. |
| 4,453,932 A | 6/1984 | Pastrone |
| 4,479,760 A | 10/1984 | Bilstad et al. |
| 4,479,762 A | 10/1984 | Bilstad et al. |
| 4,558,715 A | 12/1985 | Walton et al. |
| 4,569,378 A | 2/1986 | Bergandy |
| 4,597,412 A | 7/1986 | Stark |
| 4,623,328 A | 11/1986 | Hartranft |
| 4,628,499 A | 12/1986 | Hammett |
| 4,639,245 A | 1/1987 | Pastrone et al. |
| 4,643,713 A | 2/1987 | Viitala |
| 4,657,490 A | 4/1987 | Abbott |
| 4,662,598 A | 5/1987 | Weingarten |
| 4,662,906 A | 5/1987 | Matkovich et al. |
| 4,676,467 A | 6/1987 | Palsulich |
| 4,703,913 A | 11/1987 | Hunkapiller |
| 4,705,259 A | 11/1987 | Dolhen et al. |
| 4,710,166 A | 12/1987 | Thompson et al. |
| 4,778,451 A | 10/1988 | Kamen |
| 4,808,161 A | 2/1989 | Kamen |
| 4,826,482 A | 5/1989 | Kamen |
| 4,840,542 A | 6/1989 | Abbott |
| 4,842,584 A | 6/1989 | Pastrone |
| 4,846,636 A | 7/1989 | Danby et al. |
| 4,902,282 A | 2/1990 | Bellotti et al. |
| 4,906,260 A | 3/1990 | Emheiser et al. |
| 4,927,411 A | 5/1990 | Pastrone et al. |
| 4,950,134 A | 8/1990 | Bailey et al. |
| 4,976,162 A | 12/1990 | Kamen |
| 4,995,864 A | 2/1991 | Bartholomew et al. |
| 4,997,464 A | 3/1991 | Kopf |
| 5,002,471 A | 3/1991 | Perlov |
| 5,006,050 A | 4/1991 | Cooke et al. |
| 5,036,886 A | 8/1991 | Olsen et al. |
| 5,061,236 A | 10/1991 | Sutherland et al. |
| 5,088,515 A | 2/1992 | Kamen |
| 5,098,262 A | 3/1992 | Wecker et al. |
| 5,100,380 A | 3/1992 | Epstein |
| 5,100,699 A | 3/1992 | Roeser |
| 5,116,021 A | 5/1992 | Faust et al. |
| 5,116,316 A | 5/1992 | Sertic et al. |
| 5,146,713 A | 9/1992 | Grafius |
| 5,151,019 A | 9/1992 | Danby et al. |
| 5,167,837 A | 12/1992 | Snodgrass et al. |
| 5,171,029 A | 12/1992 | Maxwell et al. |
| 5,178,182 A | 1/1993 | Kamen |
| 5,193,990 A | 3/1993 | Kamen et al. |
| 5,211,201 A | 5/1993 | Kamen et al. |
| 5,241,985 A | 9/1993 | Faust et al. |
| 5,247,434 A | 9/1993 | Peterson et al. |
| 5,252,044 A | 10/1993 | Raines et al. |
| 5,279,556 A | 1/1994 | Goi et al. |
| 5,302,093 A | 4/1994 | Owens et al. |
| 5,324,422 A | 6/1994 | Colleran et al. |
| 5,330,425 A | 7/1994 | Utterberg |
| 5,350,357 A | 9/1994 | Kamen et al. |
| D351,470 S | 10/1994 | Scherer et al. |
| 5,353,837 A | 10/1994 | Faust |
| 5,378,126 A | 1/1995 | Abrahamson et al. |
| 5,395,351 A | 3/1995 | Munsch |
| 5,415,528 A | 5/1995 | Ogden et al. |
| 5,421,208 A | 6/1995 | Packard et al. |
| 5,421,823 A | 6/1995 | Kamen et al. |
| 5,427,509 A | 6/1995 | Chapman et al. |
| 5,431,626 A | 7/1995 | Bryant et al. |
| 5,431,627 A | 7/1995 | Pastrone et al. |
| 5,431,634 A | 7/1995 | Brown |
| 5,438,510 A | 8/1995 | Bryant et al. |
| 5,441,636 A | 8/1995 | Chevallet et al. |
| 5,445,506 A | 8/1995 | Afflerbaugh et al. |
| 5,447,286 A | 9/1995 | Kamen et al. |
| 5,462,416 A | 10/1995 | Dennehey et al. |
| 5,462,417 A | 10/1995 | Chapman |
| 5,474,683 A | 12/1995 | Bryant et al. |
| 5,478,211 A | 12/1995 | Dominiak et al. |
| 5,480,294 A | 1/1996 | Di Perna et al. |
| 5,482,438 A | 1/1996 | Anderson et al. |
| 5,482,440 A | 1/1996 | Dennehey et al. |
| 5,482,446 A | 1/1996 | Williamson et al. |
| 5,484,239 A | 1/1996 | Chapman et al. |
| 5,486,286 A | 1/1996 | Peterson et al. |
| 5,514,069 A | 5/1996 | Brown et al. |
| 5,538,405 A | 7/1996 | Patno et al. |
| 5,540,568 A | 7/1996 | Rosen et al. |
| 5,547,453 A | 8/1996 | Di Perna |
| 5,551,850 A | 9/1996 | Williamson et al. |
| 5,551,941 A | 9/1996 | Howell |
| 5,551,942 A | 9/1996 | Brown et al. |
| 5,554,013 A | 9/1996 | Owens et al. |
| 5,570,716 A | 11/1996 | Kamen et al. |
| 5,578,070 A | 11/1996 | Utterberg |
| 5,609,572 A | 3/1997 | Lang |
| 5,614,677 A | 3/1997 | Wamsiedler et al. |
| 5,628,908 A | 5/1997 | Kamen et al. |
| 5,630,710 A | 5/1997 | Tune et al. |
| 5,634,896 A | 6/1997 | Bryant et al. |
| 5,640,995 A | 6/1997 | Packard et al. |
| 5,641,405 A | 6/1997 | Keshaviah et al. |
| 5,641,892 A | 6/1997 | Larkins et al. |
| 5,643,205 A | 7/1997 | Utterberg |
| 5,658,133 A | 8/1997 | Anderson et al. |
| 5,690,602 A | 11/1997 | Brown et al. |
| D390,654 S | 2/1998 | Alsberg et al. |
| 5,713,865 A | 2/1998 | Manning et al. |
| 5,713,888 A | 2/1998 | Neuenfeldt et al. |
| 5,741,125 A | 4/1998 | Neftel et al. |
| 5,746,708 A | 5/1998 | Giesler et al. |
| 5,755,683 A | 5/1998 | Houle et al. |
| 5,764,034 A | 6/1998 | Bowman et al. |
| 5,769,387 A | 6/1998 | Perez |
| 5,771,914 A | 6/1998 | Ling et al. |
| 5,772,635 A | 6/1998 | Dastur et al. |
| 5,772,637 A | 6/1998 | Heinzmann et al. |
| 5,775,371 A | 7/1998 | Pan et al. |
| 5,782,575 A | 7/1998 | Vincent et al. |
| 5,782,805 A | 7/1998 | Meinzer et al. |
| 5,799,207 A | 8/1998 | Wang et al. |
| 5,816,779 A | 10/1998 | Lawless et al. |
| 5,840,151 A | 11/1998 | Munsch |
| 5,842,841 A | 12/1998 | Danby et al. |
| 5,843,035 A | 12/1998 | Bowman et al. |
| 5,868,696 A | 2/1999 | Giesler et al. |
| 5,873,853 A | 2/1999 | Keilman et al. |
| 5,906,598 A | 5/1999 | Giesler et al. |
| 5,921,951 A | 7/1999 | Morris |
| 5,925,011 A | 7/1999 | Faict et al. |
| 5,935,099 A | 8/1999 | Peterson et al. |
| 5,938,634 A | 8/1999 | Packard |
| 5,989,423 A | 11/1999 | Kamen |
| 5,993,174 A | 11/1999 | Konishi |
| 5,996,634 A | 12/1999 | Dennehey et al. |
| 6,013,057 A | 1/2000 | Danby et al. |
| 6,036,668 A | 3/2000 | Mathis |
| 6,036,680 A | 3/2000 | Horne et al. |
| 6,041,801 A | 3/2000 | Gray et al. |
| 6,053,191 A | 4/2000 | Hussey |
| 6,065,389 A | 5/2000 | Riedlinger |
| 6,065,941 A | 5/2000 | Gray et al. |
| 6,068,612 A | 5/2000 | Bowman et al. |
| 6,074,359 A | 6/2000 | Keshaviah et al. |
| 6,099,492 A | 8/2000 | Le Boeuf |
| 6,110,410 A | 8/2000 | Owens et al. |
| 6,118,207 A | 9/2000 | Ormerod et al. |
| 6,129,517 A | 10/2000 | Danby et al. |
| 6,132,187 A | 10/2000 | Ericson |
| 6,136,565 A | 10/2000 | Best et al. |

(56) References Cited

U.S. PATENT DOCUMENTS

| | | |
|---|---|---|
| 6,154,605 A | 11/2000 | Aonuma |
| 6,164,621 A | 12/2000 | Bouchard et al. |
| 6,165,154 A | 12/2000 | Gray et al. |
| 6,179,801 B1 | 1/2001 | Holmes et al. |
| 6,184,356 B1 | 2/2001 | Anderson et al. |
| 6,189,857 B1 | 2/2001 | Zeger et al. |
| 6,196,987 B1 | 3/2001 | Holmes et al. |
| 6,200,287 B1 | 3/2001 | Keller et al. |
| 6,208,107 B1 | 3/2001 | Maske et al. |
| 6,210,361 B1 | 4/2001 | Kamen et al. |
| 6,220,295 B1 | 4/2001 | Bouchard et al. |
| 6,223,130 B1 | 4/2001 | Gray et al. |
| 6,227,807 B1 | 5/2001 | Chase |
| 6,228,047 B1 | 5/2001 | Dadson |
| 6,231,537 B1 | 5/2001 | Holmes et al. |
| 6,234,989 B1 | 5/2001 | Brierton et al. |
| 6,250,502 B1 | 6/2001 | Cote et al. |
| 6,261,065 B1 | 7/2001 | Nayak et al. |
| 6,267,242 B1 | 7/2001 | Nagata et al. |
| 6,270,673 B1 | 8/2001 | Belt et al. |
| 6,280,406 B1 | 8/2001 | Dolecek et al. |
| 6,281,145 B1 | 8/2001 | Deguchi et al. |
| 6,284,142 B1 | 9/2001 | Muller |
| 6,285,155 B1 | 9/2001 | Maske et al. |
| 6,294,094 B1 | 9/2001 | Muller et al. |
| 6,296,450 B1 | 10/2001 | Westberg et al. |
| 6,297,322 B1 | 10/2001 | Ding et al. |
| 6,315,707 B1 | 11/2001 | Smith et al. |
| 6,316,864 B1 | 11/2001 | Ormerod |
| 6,322,488 B1 | 11/2001 | Westberg et al. |
| 6,325,775 B1 | 12/2001 | Thom et al. |
| 6,337,049 B1 | 1/2002 | Tamari |
| RE37,553 E | 2/2002 | Ciavarini et al. |
| 6,343,614 B1 | 2/2002 | Gray et al. |
| 6,348,156 B1 | 2/2002 | Vishnoi et al. |
| 6,361,518 B1 | 3/2002 | Brierton et al. |
| 6,364,857 B1 | 4/2002 | Gray et al. |
| 6,382,923 B1 | 5/2002 | Gray |
| 6,383,158 B1 | 5/2002 | Utterberg et al. |
| 6,406,276 B1 | 6/2002 | Normand et al. |
| 6,409,696 B1 | 6/2002 | Toavs et al. |
| 6,416,293 B1 | 7/2002 | Bouchard et al. |
| 6,419,822 B2 | 7/2002 | Muller et al. |
| 6,455,676 B1 | 9/2002 | Weickert et al. |
| 6,471,855 B1 | 10/2002 | Odak et al. |
| 6,481,980 B1 | 11/2002 | Vandlik et al. |
| 6,484,383 B1 | 11/2002 | Herklotz |
| 6,489,896 B1 | 12/2002 | Platt et al. |
| 6,491,656 B1 * | 12/2002 | Morris ............... 604/6.09 |
| 6,494,694 B2 | 12/2002 | Lawless et al. |
| 6,497,674 B1 | 12/2002 | Steele et al. |
| 6,497,676 B1 | 12/2002 | Childers et al. |
| 6,503,062 B1 | 1/2003 | Gray et al. |
| 6,514,225 B1 | 2/2003 | Utterberg et al. |
| 6,519,569 B1 | 2/2003 | White et al. |
| 6,520,747 B2 | 2/2003 | Gray et al. |
| 6,524,231 B1 | 2/2003 | Westberg et al. |
| 6,529,573 B2 | 3/2003 | Olsher et al. |
| 6,537,445 B2 | 3/2003 | Muller |
| 6,542,761 B1 | 4/2003 | Jahn et al. |
| 6,558,343 B1 | 5/2003 | Neftel |
| 6,572,604 B1 | 6/2003 | Platt et al. |
| 6,592,542 B2 | 7/2003 | Childers et al. |
| 6,595,948 B2 | 7/2003 | Suzuki et al. |
| 6,603,229 B1 | 8/2003 | Toye, IV |
| 6,604,908 B1 | 8/2003 | Bryant et al. |
| 6,645,166 B2 | 11/2003 | Scheunert et al. |
| 6,645,177 B1 | 11/2003 | Shearn |
| 6,648,861 B2 | 11/2003 | Platt et al. |
| 6,663,359 B2 | 12/2003 | Gray |
| 6,670,323 B1 | 12/2003 | Looker et al. |
| 6,672,841 B1 | 1/2004 | Herklotz et al. |
| 6,695,593 B1 | 2/2004 | Steck et al. |
| 6,695,803 B1 | 2/2004 | Robinson et al. |
| 6,709,417 B1 | 3/2004 | Houle et al. |
| 6,716,004 B2 | 4/2004 | Vandlik et al. |
| 6,723,062 B1 | 4/2004 | Westberg et al. |
| 6,725,726 B1 | 4/2004 | Adolfs et al. |
| 6,726,656 B2 | 4/2004 | Kamen et al. |
| 6,730,055 B2 | 5/2004 | Bainbridge et al. |
| 6,743,201 B1 | 6/2004 | Dönig et al. |
| 6,746,514 B2 | 6/2004 | Bedingfield et al. |
| 6,749,403 B2 | 6/2004 | Bryant et al. |
| 6,752,172 B2 | 6/2004 | Lauer |
| 6,755,801 B2 | 6/2004 | Utterberg et al. |
| 6,758,975 B2 | 7/2004 | Peabody et al. |
| 6,759,007 B1 | 7/2004 | Westberg et al. |
| 6,764,460 B2 | 7/2004 | Dolecek et al. |
| 6,764,761 B2 | 7/2004 | Eu et al. |
| 6,768,425 B2 | 7/2004 | Flaherty et al. |
| 6,774,517 B2 | 8/2004 | Kowalski et al. |
| 6,790,014 B2 | 9/2004 | Bowen |
| 6,790,195 B2 | 9/2004 | Steele et al. |
| 6,790,198 B1 | 9/2004 | White et al. |
| 6,800,054 B2 | 10/2004 | Westberg et al. |
| 6,808,369 B2 | 10/2004 | Gray et al. |
| 6,814,547 B2 | 11/2004 | Childers et al. |
| 6,821,432 B2 | 11/2004 | Metzner |
| 6,828,125 B1 | 12/2004 | Hoffman et al. |
| 6,846,161 B2 | 1/2005 | Kline et al. |
| 6,852,090 B2 | 2/2005 | Burbank et al. |
| 6,869,538 B2 | 3/2005 | Yu et al. |
| 6,905,479 B1 | 6/2005 | Bouchard et al. |
| 6,929,751 B2 | 8/2005 | Bowman, Jr. et al. |
| 6,939,111 B2 | 9/2005 | Huitt et al. |
| 6,949,079 B1 | 9/2005 | Westberg et al. |
| 6,953,323 B2 | 10/2005 | Childers et al. |
| 6,957,952 B1 | 10/2005 | Steck et al. |
| 6,984,218 B2 | 1/2006 | Nayak et al. |
| 7,021,148 B2 | 4/2006 | Kuhn et al. |
| 7,033,539 B2 | 4/2006 | Krensky et al. |
| 7,041,076 B1 | 5/2006 | Westberg et al. |
| 7,044,432 B2 | 5/2006 | Beden et al. |
| 7,049,406 B2 | 5/2006 | Weickert et al. |
| 7,083,719 B2 | 8/2006 | Bowman, Jr. et al. |
| 7,087,036 B2 | 8/2006 | Busby et al. |
| 7,107,837 B2 | 9/2006 | Lauman et al. |
| 7,115,107 B2 | 10/2006 | Delnevo et al. |
| 7,115,228 B2 | 10/2006 | Lundtveit et al. |
| 7,147,613 B2 | 12/2006 | Burbank et al. |
| 7,153,286 B2 | 12/2006 | Busby et al. |
| 7,160,087 B2 | 1/2007 | Fathallah et al. |
| 7,166,231 B2 | 1/2007 | Westberg et al. |
| 7,175,606 B2 | 2/2007 | Bowman, Jr. et al. |
| 7,195,607 B2 | 3/2007 | Westberg et al. |
| 7,211,560 B2 | 5/2007 | Looker et |
| 7,232,435 B2 | 6/2007 | Hildebrand et al. |
| 7,236,936 B2 | 6/2007 | White et al. |
| 7,238,164 B2 | 7/2007 | Childers et al. |
| 7,255,680 B1 | 8/2007 | Gharib |
| 7,258,534 B2 | 8/2007 | Fathallah et al. |
| 7,267,661 B2 | 9/2007 | Susi |
| 7,273,465 B2 | 9/2007 | Ash |
| 7,306,578 B2 | 12/2007 | Gray et al. |
| 7,338,472 B2 | 3/2008 | Shearn |
| 7,345,025 B2 | 3/2008 | Symonds et al. |
| 7,347,836 B2 | 3/2008 | Peterson et al. |
| 7,390,311 B2 | 6/2008 | Hildebrand et al. |
| 7,398,183 B2 | 7/2008 | Holland et al. |
| 7,399,637 B2 | 7/2008 | Wright et al. |
| 7,404,809 B2 | 7/2008 | Susi |
| 7,410,475 B2 | 8/2008 | Krensky et al. |
| 7,422,905 B2 | 9/2008 | Clague et al. |
| 7,454,314 B2 | 11/2008 | Holland et al. |
| 7,490,021 B2 | 2/2009 | Holland et al. |
| 7,500,962 B2 | 3/2009 | Childers et al. |
| 7,517,387 B2 | 4/2009 | Chevallet et al. |
| 7,553,295 B2 | 6/2009 | Susi |
| 7,556,616 B2 | 7/2009 | Fathallah et al. |
| 7,575,564 B2 | 8/2009 | Childers |
| 7,618,948 B2 | 11/2009 | Kaemmerer |
| 7,645,258 B2 | 1/2010 | White et al. |
| 7,648,627 B2 | 1/2010 | Beden et al. |
| 7,654,976 B2 | 2/2010 | Peterson et al. |

(56) References Cited

U.S. PATENT DOCUMENTS

| | | |
|---|---|---|
| 7,662,286 B2 | 2/2010 | Childers et al. |
| 7,699,966 B2 | 4/2010 | Qin et al. |
| 7,717,682 B2 | 5/2010 | Orr |
| 7,789,849 B2 | 9/2010 | Busby et al. |
| 7,815,595 B2 | 10/2010 | Busby et al. |
| 8,038,640 B2 | 10/2011 | Orr |
| 8,197,231 B2 | 6/2012 | Orr |
| 8,197,439 B2 | 6/2012 | Wang et al. |
| 8,206,338 B2 | 6/2012 | Childers et al. |
| 8,292,594 B2 | 10/2012 | Tracey et al. |
| 8,366,921 B2 | 2/2013 | Beden et al. |
| 2001/0034502 A1 | 10/2001 | Moberg |
| 2001/0037763 A1 | 11/2001 | Deguchi et al. |
| 2002/0048581 A1 | 4/2002 | King |
| 2002/0062109 A1 | 5/2002 | Lauer |
| 2002/0072718 A1 | 6/2002 | Brugger et al. |
| 2002/0107474 A1 | 8/2002 | Noack |
| 2002/0147423 A1 | 10/2002 | Burbank et al. |
| 2003/0018395 A1 | 1/2003 | Crnkovich et al. |
| 2003/0028144 A1 | 2/2003 | Duchon et al. |
| 2003/0029451 A1 | 2/2003 | Blair et al. |
| 2003/0042181 A1 | 3/2003 | Metzner |
| 2003/0100882 A1 | 5/2003 | Beden et al. |
| 2003/0136189 A1 | 7/2003 | Lauman et al. |
| 2003/0200812 A1 | 10/2003 | Kuhn et al. |
| 2003/0204162 A1 | 10/2003 | Childers et al. |
| 2003/0217957 A1 | 11/2003 | Bowman et al. |
| 2003/0217961 A1 | 11/2003 | Hopping |
| 2003/0217975 A1 | 11/2003 | Yu et al. |
| 2003/0218623 A1 | 11/2003 | Krensky et al. |
| 2003/0220599 A1 | 11/2003 | Lundtveit et al. |
| 2003/0220605 A1 | 11/2003 | Bowman et al. |
| 2003/0220607 A1 | 11/2003 | Busby et al. |
| 2003/0220608 A1 | 11/2003 | Huitt et al. |
| 2003/0220609 A1 | 11/2003 | Childers et al. |
| 2003/0220627 A1 | 11/2003 | Distler et al. |
| 2004/0001766 A1 | 1/2004 | Maianti et al. |
| 2004/0010223 A1 | 1/2004 | Busby et al. |
| 2004/0019313 A1 | 1/2004 | Childers et al. |
| 2004/0019320 A1 | 1/2004 | Childers et al. |
| 2004/0031756 A1 | 2/2004 | Suzuki et al. |
| 2004/0064080 A1 | 4/2004 | Cruz et al. |
| 2004/0067161 A1 | 4/2004 | Axelsson |
| 2004/0082903 A1 | 4/2004 | Micheli |
| 2004/0084647 A1 | 5/2004 | Beden et al. |
| 2004/0135078 A1 | 7/2004 | Mandro et al. |
| 2004/0156745 A1 | 8/2004 | Vandlik et al. |
| 2004/0195190 A1 | 10/2004 | Min et al. |
| 2004/0238416 A1 | 12/2004 | Burbank et al. |
| 2005/0054968 A1 | 3/2005 | Giannella |
| 2005/0230292 A1 | 10/2005 | Beden et al. |
| 2006/0002823 A1 | 1/2006 | Feldstein |
| 2006/0079826 A1 | 4/2006 | Beden et al. |
| 2006/0195064 A1 | 8/2006 | Plahey et al. |
| 2007/0112297 A1 | 5/2007 | Plahey et al. |
| 2007/0149913 A1 | 6/2007 | Busby et al. |
| 2007/0193940 A1 | 8/2007 | Duchamp et al. |
| 2007/0213651 A1 | 9/2007 | Busby et al. |
| 2007/0213653 A1 | 9/2007 | Childers et al. |
| 2007/0269340 A1 | 11/2007 | Dannenmaier et al. |
| 2008/0033346 A1 | 2/2008 | Childers et al. |
| 2008/0077068 A1 | 3/2008 | Orr |
| 2008/0208103 A1 | 8/2008 | Demers et al. |
| 2008/0216898 A1 | 9/2008 | Grant et al. |
| 2008/0253912 A1 | 10/2008 | Demers et al. |
| 2009/0004033 A1 | 1/2009 | Demers et al. |
| 2009/0099498 A1 | 4/2009 | Demers et al. |
| 2009/0137940 A1 | 5/2009 | Orr |
| 2010/0241062 A1 | 9/2010 | Morris et al. |
| 2011/0092895 A1 | 4/2011 | Yardimci et al. |
| 2011/0125085 A1 | 5/2011 | McGill et al. |
| 2011/0137237 A1 | 6/2011 | Prisco et al. |
| 2012/0065581 A1 | 3/2012 | Childers et al. |
| 2012/0123322 A1 | 5/2012 | Scarpaci et al. |
| 2012/0224984 A1 | 9/2012 | Orr |
| 2012/0308412 A1 | 12/2012 | Rochat |
| 2013/0184638 A1 | 7/2013 | Scarpaci et al. |

FOREIGN PATENT DOCUMENTS

| | | |
|---|---|---|
| DE | 2827648 | 1/1979 |
| DE | 4006785 | 9/1990 |
| DE | 4336336 | 5/1994 |
| DE | 198 37 667 | 3/2000 |
| DE | 19919572 A1 | 11/2000 |
| DE | 100 42 324 | 2/2002 |
| DE | 100 46 651 | 4/2002 |
| DE | 19919572 C2 | 4/2002 |
| DE | 100 53 441 | 5/2002 |
| DE | 101 57 924 | 5/2002 |
| DE | 69618766 | 8/2002 |
| DE | 101 43 137 | 4/2003 |
| DE | 102007059239 A1 | 6/2009 |
| EP | 0314379 | 8/1991 |
| EP | 0410125 B1 | 8/1993 |
| EP | 0728509 | 8/1996 |
| EP | 0848193 | 6/1998 |
| EP | 0 947 814 B2 | 10/1999 |
| EP | 0 956 876 A1 | 11/1999 |
| EP | 1529545 | 5/2005 |
| GB | 1483702 | 8/1977 |
| GB | 2331796 | 6/1999 |
| JP | 0396850 A | 4/1991 |
| JP | 04-191755 | 7/1992 |
| JP | 06-154314 | 6/1994 |
| JP | 06-002650 | 11/1994 |
| JP | 08028722 | 2/1996 |
| JP | 11-347115 | 12/1999 |
| JP | 2000-070358 | 3/2000 |
| JP | 2000346214 | 12/2000 |
| WO | WO 84/02473 | 7/1984 |
| WO | WO8601115 A1 | 2/1986 |
| WO | WO 94/20155 | 9/1994 |
| WO | WO9625064 A3 | 9/1996 |
| WO | WO 97/16214 | 5/1997 |
| WO | WO 97/37703 | 10/1997 |
| WO | WO 98/22165 | 5/1998 |
| WO | WO9822167 A1 | 5/1998 |
| WO | WO 00/23140 | 4/2000 |
| WO | WO 00/33898 | 6/2000 |
| WO | WO 01/17605 | 3/2001 |
| WO | 0225146 A1 | 3/2002 |
| WO | WO 02/25225 | 3/2002 |
| WO | 2009071069 A1 | 6/2009 |
| WO | WO2009071069 A1 | 6/2009 |
| WO | WO2011045167 A1 | 4/2011 |

OTHER PUBLICATIONS

Gambro®, "Prisma® HF 1000, For Increased Filtration Capacity", © Aug. 2001, Gambro Renal Products, Inc., Lakewood, CO, 2 pp.
Gambro®, "Prisma® M60 and M100 Pre-Pump Infusion Sets—Introducing: The unique solution that enables Physicians to choose a predilution method that meets the needs of their patients", © 2004, Gambro Inc., Lakewood, CO, 4 pp.
Gambro®, "Prismaflex™ anticipating critical care needs and taking our innovative response . . . to new heights," © 2004, Gambro Inc., Lakewood, CO, 8 pp.
Glenn Avolio, "Principles of Rotary Optical Encoders," Sensors Journal of Machine Perception, vol. 10, No. 4, pp. 10-18, 1993.
Manns, Markus et al., "The acu-men: A new device for continuous renal replacement therapy in acute renal failure," Kidney International, vol. 54, pp. 268-274, 1998.
Liberty Cycler Operator's Manual, 2003-2004.
Newton IQ Cycler Operator Manual, Part No. 470203 Rev. F, 2000-2006.
Operator's Instructions, Fresenius 90/2 Peritoneal Therapy Cycler, Part No. 470016 Rev. B, 1991.
Operator's Manual, Serena, Program Version 3.xx—English.
Sleep Safe Operating Instructions, Software Version 0.9, Part No. 677 805 1.

(56) References Cited

OTHER PUBLICATIONS

Sleep Safe Technical Manual, Part No. 677 807 1.
Bolegoh, Gordon, "Pumps: Reference Guide", p. 24, 3rd edition, 2001.
Ronco et al., "Evolution of Machines for Automated Peritoneal Dialysis", in Automated Peritoneal Dialysis, Contributions to Nephrology, vol. 129, pp. 142-161, 1999.
Sleep Safe Operating Instructions, Software Version 0.5, Apr. 1999.
Sleep Safe Operating Instructions, Software Version 1.0, Oct. 2000.
Sleep Safe Technical Manual, Dec. 2001.
Sleep Safe Operating Instructions, Jan. 2002.
Sleep Safe Communicating Therapy, Mar. 1998.
Sleep Safe Kommunizierte Therapie, May 1998.
Innovative Technologies in Peritoneal Dialysis, Sleep Safe Concept, Oct. 13, 1999 (4 attachments).
TL™ Pump Brochure, TL Systems Corporation.

* cited by examiner

MEDICAL FLUID CASSETTES AND RELATED SYSTEMS

CROSS-REFERENCE TO RELATED APPLICATIONS

This application is a continuation application of and claims priority to U.S. application Ser. No. 12/627,043, filed on Nov. 30, 2009 now U.S. Pat. No. 8,142,653, which is a continuation application of and claims priority to U.S. application Ser. No. 10/516,528, filed on Dec. 2, 2004, now U.S. Pat. No. 7,648,627, which is a nationalization of PCT/EP03/05377, filed on May 22, 2003 and published in German, which claims priority under 35 U.S.C. §119(a) to DE 102 24 750.1, filed on Jun. 4, 2002.

TECHNICAL FIELD

The invention relates to an apparatus for the treatment of a medical fluid comprising a fluid treatment machine and a cassette insertable therein substantially consisting of a rigid base body of the cassette with fitted chambers and passages and a foil covering them.

BACKGROUND

Cassettes are used in medical engineering, in particular to convey dialysis fluid, blood and the like.

A cassette can include a base body with fitted chambers and passages which is closed by a flexible foil to cover the passages and chambers. The cassette can be inserted into a special receiving chamber, e.g., in a dialysis machine. This chamber can, for example, be opened via a pivotable door. The cassette can be inserted into the chamber, with the flexible foil lying opposite a corresponding mating piece at the machine so that the cassette can be operated with the aid of actuators and sensors on the machine side.

Conventional extracorporeal blood circuits or blood tubing systems are usually present in a differential construction. This means that a functional division onto different components is present. Such components (e.g., bubble traps, flow chambers or injection positions) are connected to one another by tubes and are as a rule connected individually to the respective dialysis machine. The design of such blood tubing systems is very complex in manufacture and handling, with the corresponding effort naturally being extremely time consuming with more complex systems such as an online hemodiafiltration.

On the other hand, conventional extracorporeal blood circuits which are installed in this differential construction have the advantage that they can be designed substantially more flexibly for the respective treatment depending on the demand. Previously known apparatuses for the use of cassettes typically were only usable for a very specific application.

SUMMARY

Certain aspects of the invention relate to a generic apparatus comprising a fluid treatment machine and a cassette insertable therein such that a large flexibility for different applications is made possible while maintaining the fast and simple exchangeability.

In some aspects of the invention, actuators and sensors are arranged in a generic apparatus for the treatment of a medical fluid for the operation of the apparatus with an inserted cassette such that cassettes are insertable in different integration shapes.

Due to the clearly defined arrangement of corresponding sensors and actuators, cassettes of different complexity can be inserted into the fluid treatment machine in accordance with the desired application. It is therefore not necessary to provide different apparatus for different applications.

A cassette for a standard hemodialysis can thus be insertable here, for example. The corresponding pump chambers, measuring sensors and further actuators, such as valves, etc., are provided at pre-determined locations in the fluid treatment machine. Additional pumps, actuators, valves, etc. are provided in the fluid treatment machine which do not have to be actuated when the cassette is used for standard hemodialysis. They are, for example, only in use when a cassette is used for online hemodiafiltration or online hemofiltration. Further passages, pump chambers, etc. are provided at corresponding positions in the corresponding cassettes which are associated with these actuators, pumps or valves. Furthermore, a cassette for an acute dialysis treatment can be inserted in which in turn the pumps, actuators and valves provided on the side of the fluid treatment machine are associated with corresponding pumping chambers, passages, etc. The associated control electronics can be selected depending on the inserted cassette for the control of the pumps, actuators, sensors, etc.

DESCRIPTION OF DRAWINGS

Details and advantages of the invention will be explained in more detail by way of example in the following with reference to the Figures. There are shown.

DETAILED DESCRIPTION

Figure 1:
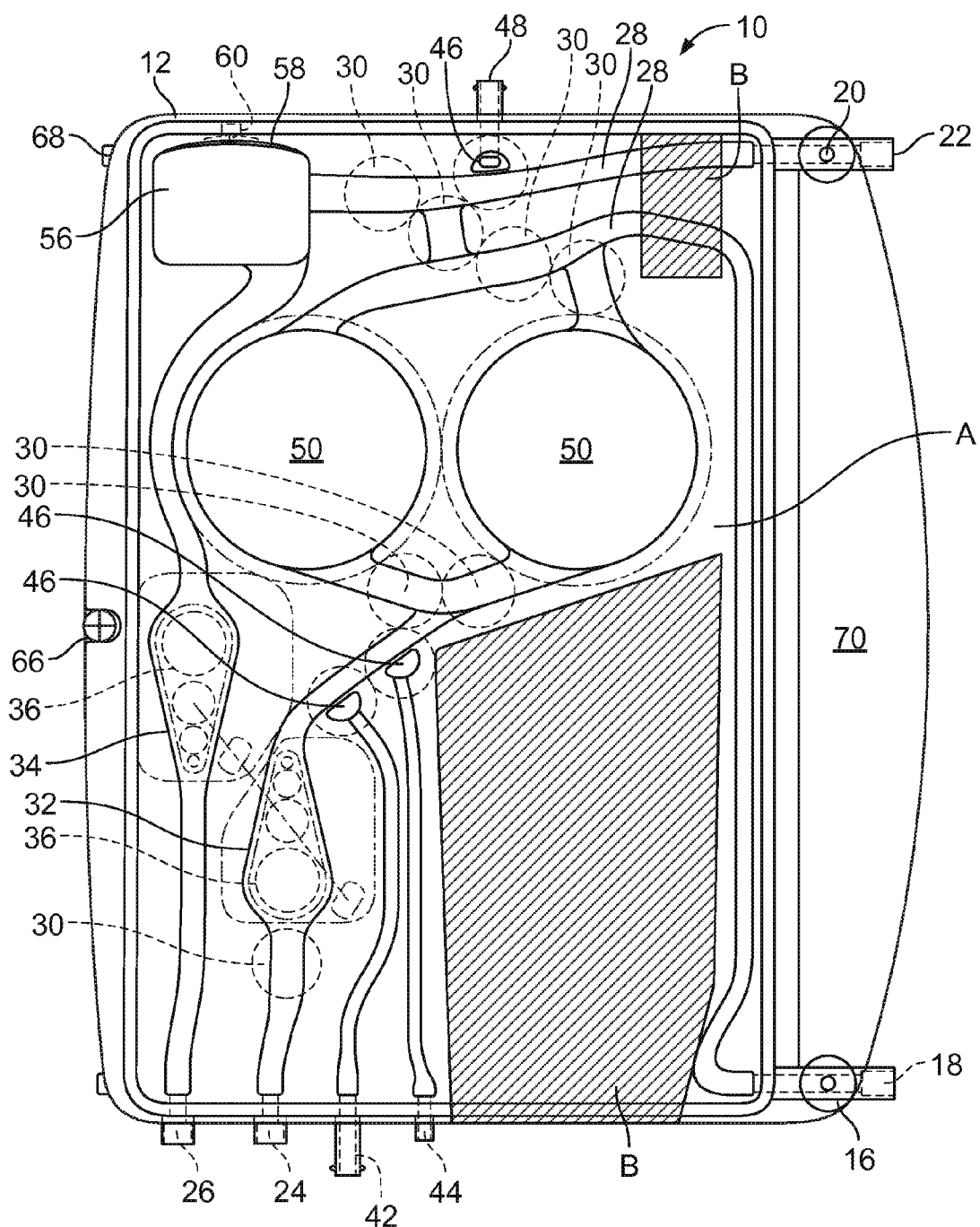
FIG. 1: a schematic plan view of a cassette for standard hemodialysis.
Figure 2:
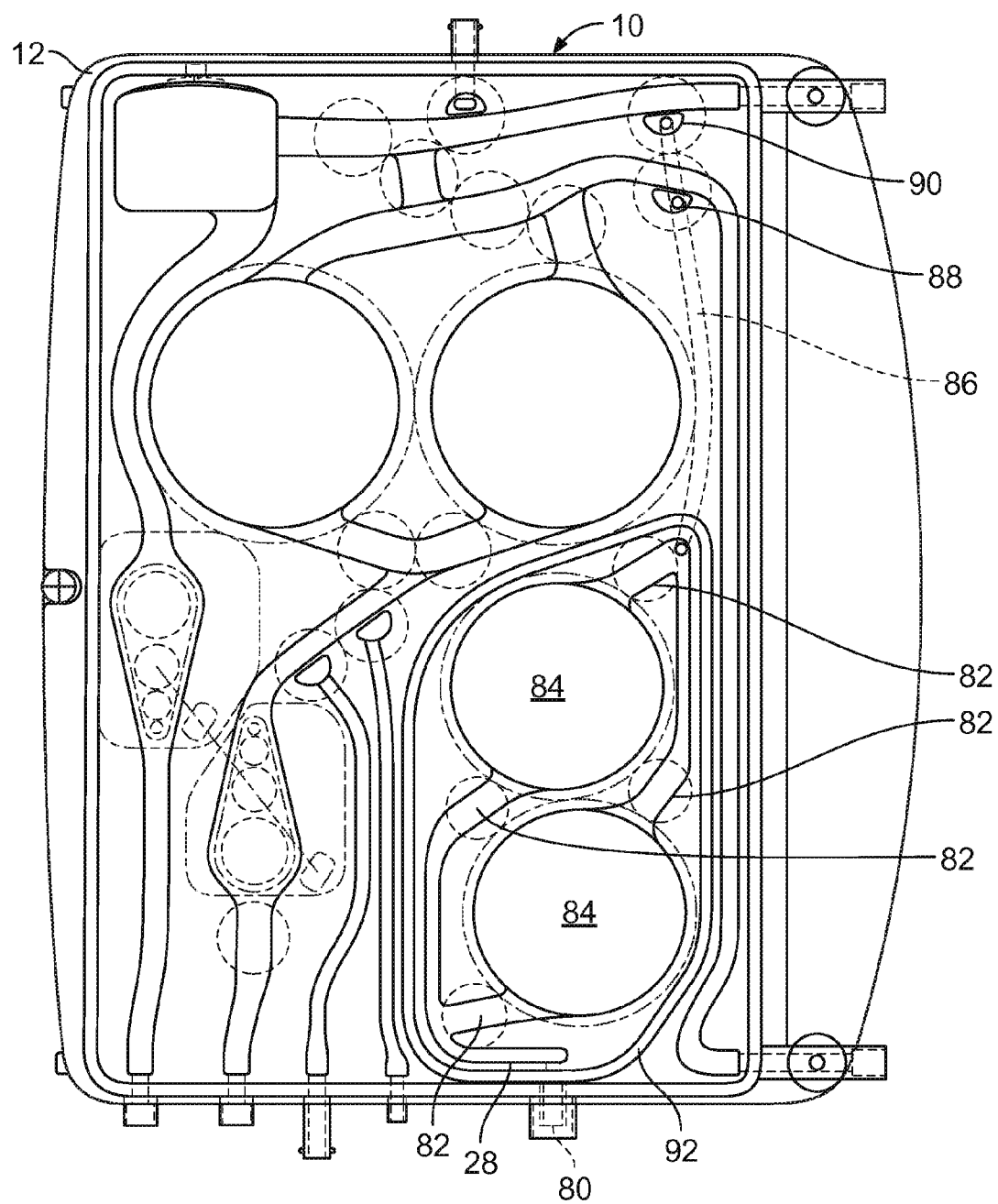
FIG. 2: a schematic plan view of a cassette in accordance with the invention according to a further embodiment of the invention for use in online hemodiafiltration or online hemofiltration.

In FIG. 1, a cassette 10 in accordance with an embodiment of the present invention is shown which can be used for standard hemodialysis. In FIG. 1, the surface of the cassette 10 is divided into a hatched region B (two partial areas) and a non-hatched region A. Both the surface of the cassette 10 and the surface of an associated machine block 108 (shown in FIG. 7) are divided into the covering surface regions A and B. Components of actuators or sensors to be coupled, which are common to all cassettes as basic variants (e.g., all the cassettes for standard hemodialysis) are accommodated in the surface region A (not hatched in FIG. 1), and the surface region B denotes a region in which actuators or sensors to be used optionally are provided in the machine block 108 (shown in FIG. 7). As discussed below, FIG. 2 illustrates a cassette that includes operable components in a region corresponding to a surface region B.

The cassette consists of a base body 12 of a cassette which consists of polypropylene in the embodiment shown here. A cover foil 14 (shown in FIGS. 10, 12, 13, 17, and 18) consisting, for example, of a polyolefin elastomer mixture, is applied to the base body 12 of the cassette 10. The passages and recesses, which will be looked at in more detail later, are covered by this cover foil 14. An arterial injection septum 16 is provided in the arterial line 18 to the dialyzer and a venous injection septum 20 is provided in the venous line 22 to the dialyzer. The dialyzer itself and the corresponding tube connection are not shown in any more detail in the embodiment shown here. Reference number 24 designates the blood inlet from the patient and reference number 26 designates the blood outlet to the patient. The respective tubes, which likewise consist of a polyolefin elastomer mixture, are also not shown here for reasons of simplification. Passages 28 are recessed in the base body 12 of the cassette 10. They are acted on by a row of valves 30.

These valves 30 have a valve body with a pressure passage and a sealing cap which cooperates with the valve body such that it closes the end of the pressure passage on the valve body side with respect to the environment, with a pressure space being able to be built up between the pressure passage and the sealing cap so that the sealing cap has a deformable sealing region for entry into the fluid passage in order to close this as required.

Figure 14:
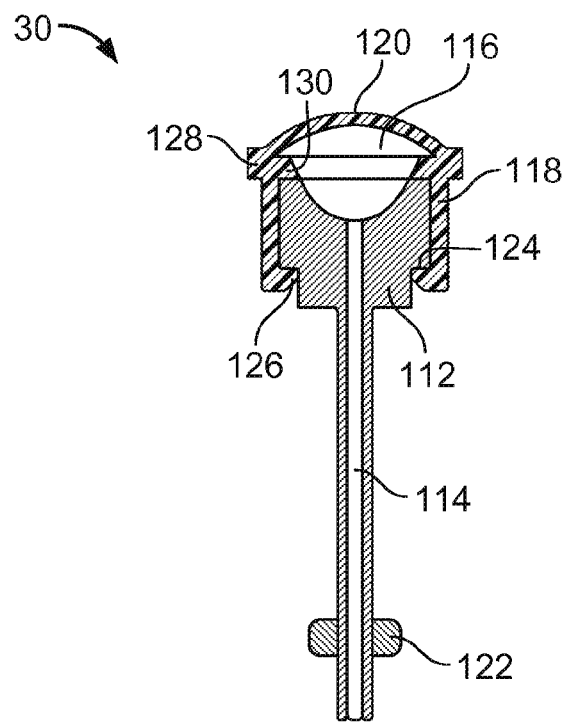
FIG. 14: a cross-sectional view of a valve.

FIG. 14 shows one of the valves 30 in a sectional view, which is rotation-symmetric about a vertical axis. The valve 30 includes a valve body 112 with a pressure channel 114, which ends in a pressure chamber 116. A sealing cap 118 with a deformable area 120, which bounds the pressure chamber 116, is placed over the valve body 112.

The pressure channel 114 of the valve body 112 is elongated, so that it can be inserted, for example, through the body or a wall of a counterpart of the disposable cassette 10 on the device side (i.e., through the machine block 108) and can be screwed down with a lock nut 122. A thread is provided on the outer wall of the portion of the valve body 112 that forms the pressure channel 114 to allow the lock nut 122 to secure the valve body 112 to the machine block 108. The valve body 112 has sealing surfaces 124 for sealing the valve body 112 in the machine block 108. The sealing cap 118 includes protruding bulges 126, which surround the valve body 112 in such a way that they lie adjacent to the sealing surfaces 124 and are pressed when the valve 30 is assembled.

Still referring to FIG. 14, the upper area of the valve 30 is the area on the fluid passage side (i.e., the side nearest the cassette 10). A projection 130 of the sealing cap 118 lies on the end of the valve body 112, on the fluid passage side. A shoulder 128 of the sealing cap 118 is provided to ensure that the sealing cap 118 fits into its associated fluid passage in the cassette 10.

Figure 15:
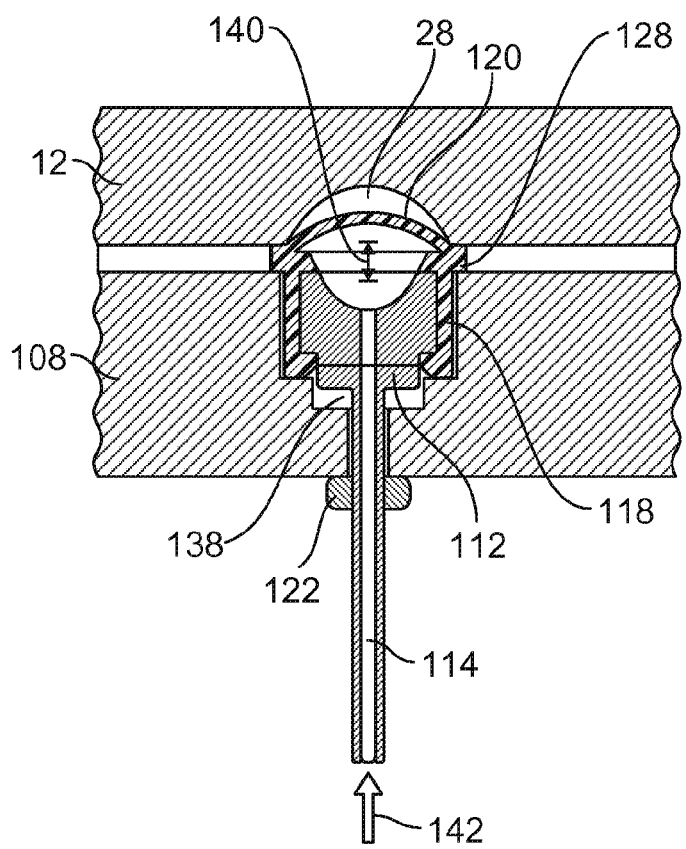
FIG. 15: a diagrammatic view of the valve of FIG. 14 in use in a disposable cartridge.

The valve 30 is shown diagramatically in use in FIG. 15. The base body 12 of the disposable cassette 10 in which liquid passages 28 are formed is shown in diagrammatic representation. The corresponding counterpart of the disposable cartridge body on the device side (i.e., the machine block 108) is shown pressed against the cassette 10.

The valve 30 is inserted into a suitably shaped housing (e.g., recess) 138 of the machine block 108 and screwed down with the lock nut 122. The shoulder 128 lies adjacent to the edges of the liquid passage 28. The movement of the deformable area 120 when an excess pressure or partial vacuum is applied or with venting of the pressure channel 114 is indicated by arrow 140. Reference number 142 indicates the direction in which the pressure is applied in order to close the valve 30. As shown in FIG. 15, the housing 138 in the machine block 108 is rotation-symmetric about the pressure channel 114 of the valve 30, and the liquid passage 28 extends perpendicular to the plane of the figure.

A cut-out for accommodating the shoulder 128 can be provided either in the base body 12 of the cassette 10 or in the machine block 108. It is also possible for the shoulder 128 to be accommodated in a suitable opening in a cover mat located between the cassette 10 and the machine block 108.

For the sake of clarity, FIG. 15 does not show the cover foil 14 of the cassette 10, which closes off the fluid passage 28 against the surroundings. The cover foil 14 (shown in FIGS. 10, 12, 13, 17, and 18) can be fixed on the side of the base body 12 of the cassette 10 that is pressed against the machine block 108. The cover foil 14 is sufficiently flexible so that it can follow the deformation of the deformable area 120 of the sealing cap 118 of the valve 130.

For the operation of the valve 30 with the cassette 10, the valve body 112 is inserted through the housing 138 of the machine block 108, so that the pressure channel 114 extends through the machine block 108. The lock nut 122 is tightened up so that the protruding bulges 126 create a seal between the valve body 112 and the machine block 108. By simply screwing the lock nut 122 onto the valve body 112, a tight and reliable connection of the valve 30 with the machine block 108 is thus provided.

The machine block 108 with the valve 30 is pressed against the cassette 10, whereby the shoulders 128 of the sealing cap 118 fit tightly with the edges of the liquid passage 28. By pressing the machine block 108 against the disposable cassette 10, several valves 30 can be simultaneously fitted into their corresponding liquid passages 28 at the desired points.

The dialysis liquid, for example, flows through the fluid passage 28 when the valve 30 is in the opened state. If excess pressure is applied via the pressure channel 114 in the direction of the arrow 142, the deformable area 120 of the sealing cap 118 is deformed into the liquid passage 28 until the valve 30 is finally closed. The loading on the sealing cap 118 is reduced by the projection 130 of the sealing cap 118, without the movement of the deformable area 120 being significantly impaired. The cover foil 14 of the cassette 10 is deformed together with the sealing cap 118 into the liquid passage 28.

If the fluid passage 28 is to be opened again, the pressure channel 114 is vented and the deformable area 120 of the sealing cap 118 is relaxed. By applying a partial vacuum to the pressure channel 114, the deformable area 120 is placed against the convex curvature of the pressure chamber 116 and correspondingly increases the cross-section of the fluid passage 28. By simply applying or removing a pressurization to the pressure channel 114, therefore, the flow rate through the fluid passage 28 can be controlled.

When the disposable cartridge is removed, the valve 30 can be removed or replaced simply by loosening lock nut 122, e.g., for maintenance or in the event of malfunction.

The sealing cap 118 is a simple low-cost shaped part, which on account of its closed design can easily be cleaned and thus satisfies the hygiene requirements in dialysis, but which can also easily be replaced when necessary.

When the disposable cassette 10 is again compressed between the machine block 108 and the base body 12, the valve 30 fits into the fluid passage 28 very well by pressing the shoulder 128 with the edge of the fluid passage 28. On account of the elastic stretching of the deformable area 120 of the sealing cap 118, there is a very good tolerance compensation both in the depth of the fluid passage 28 as well as in respect of lateral misalignment, without a significant additional expenditure of force. The deformable area 120 guarantees that only small forces are required to block the fluid passage 28.

Other details regarding the valves 30 and their operation with disposable cartridges, such as the cassette 10 described above, are discussed in DE 100 46 651, which is incorporated by reference herein.

Figure 11:
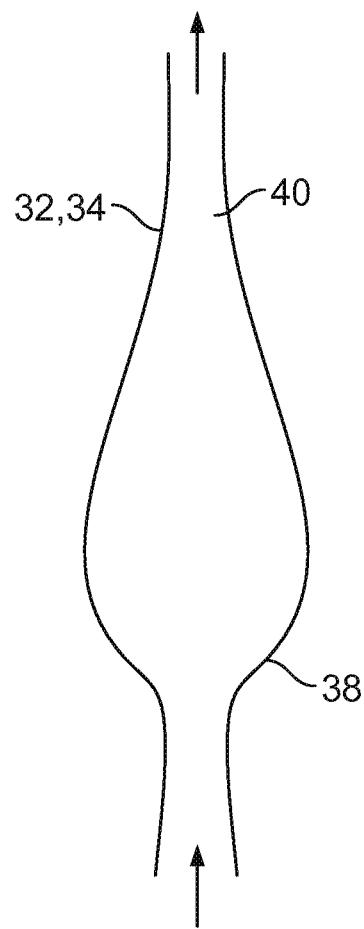
FIG. 11: a detailed view of a contour of a measuring chamber in a cassette in accordance with one of the aforesaid embodiment variants.

Referring again to FIG. 1, an arterial measuring chamber 32 and a venous measuring chamber 34 are furthermore recessed in the base body 12 of the cassette 10. The basic design of these measuring chambers is shown in FIG. 11. Referring to FIG. 11, the flow direction of the fluid, i.e., of the blood through the chambers 32, 34, is indicated by the arrows. The measuring chambers 32 and 34 have a widened passage section to be able to receive the sensors 36. The contour of the measuring chambers 32, 34 corresponds to a diffuser nozzle geometry such as is shown in FIG. 11. A diffuser 38, which runs out in a nozzle 40, is arranged in the region of the inflow region of the fluid. The widened cross-section in the diffuser 38 is relatively rapid in comparison to the narrowed cross-section in the nozzle 40. The sensors 36, which are made in the form of multi-functional sensors, are arranged in the region of the arterial or venous measuring chamber 32, 34.

More specifically, each of the sensors 36 for measuring selected parameters of the medical fluid passing in the arterial and venous measuring chambers 32, 34 is disposed on a measurement plate that has a peripheral seal along its outer edge and that is in contact with the flexible membrane (i.e., the foil 14). The measurement plate has an inlet that leads to the foil 14 so that a vacuum can be established between the measurement plate and the foil 14.

Several sensors can be mounted on the measurement plate, and since the flexible membrane (i.e., the foil 14) can be brought in close contact with the measurement plate, the medical fluids are separated from the sensors on the measurement plate only by the foil 14. Because of the peripheral seal disposed on the measurement plate, the foil 14 can be brought in close contact with the underside of the measurement plate by applying a vacuum, so that very close contact can be established between the sensors and the medical fluid in the measurement chamber. The contact surface of at least one of the sensors is preferably flush with the underside of the measurement plate, so that it is possible to establish direct measurement contact between the respective sensor and the flexible membrane.

Because of advances in miniaturization and integration technology of sensors, it is possible to arrange multiple sensors on an area a few square centimeters in size. Each respective sensor is preferably mounted in a recess in the measurement plate, with the measurement surface of the sensor being in flush contact with the underside of the measurement plate. The sensors are preferably securely glued to the measurement plate.

For example, a pressure sensor and a temperature sensor may be used. Pressure sensors have become available formed on individual semiconductor chips due to advances in integration of Microsystems, so that the chips carrying the sensor are only a few square millimeters in size. Because the sensor surface can be brought in direct contact with the foil 14, it is possible to measure both positive and negative pressures. As a result, the thermal energy balance and the venous pressure in a dialysis machine can be measured with the pressure sensor and the temperature sensor.

In some implementations, the seal of the measurement plate is made of a rubber ring which is inserted into a groove in the measurement plate and projects slightly above the edge of the measurement plate. As soon as a vacuum is established between the membrane (i.e., the foil 14) and the measurement plate, the foil 14 is pressed tightly against the underside of the measurement plate by the ambient air pressure, and the seal guarantees that no additional air can flow into the area between the measurement plate and the foil 14.

The measurement plate can be made of a metal disk into which the respective sensors are inserted. In some implementations, the metal disk is kept at a constant temperature by, for example, Peltier elements. This design permits a more accurate temperature measurement of the medical fluid.

Before performing the individual measurements, a vacuum is first applied to the inlet so that the film (i.e., the foil 14) is placed in close contact with the sensors. Then, the sensors are activated by a control unit (not shown), so that the respective measurements can begin.

The above-described sensor arrangement is described in greater detail in DE 198 37 667, which is incorporated by reference herein.

Referring again to FIG. 1, an arterial port 42 and a heparin port 44 are provided at the cassette, which are each connected via corresponding passages to the passage carrying the arterial blood in each case via phantom valves 46. The phantom valves 46 are used in the cassette 10 in accordance with the invention instead of conventional open T-branches. In these phantom valves, the passage wall is not interrupted from the aspect of the main blood flow. Reference number 48 designates a venous port which likewise opens into a blood-carrying passage 28, here in the venous part of the blood-carrying passages, via a phantom valve 46.

Figure 16:
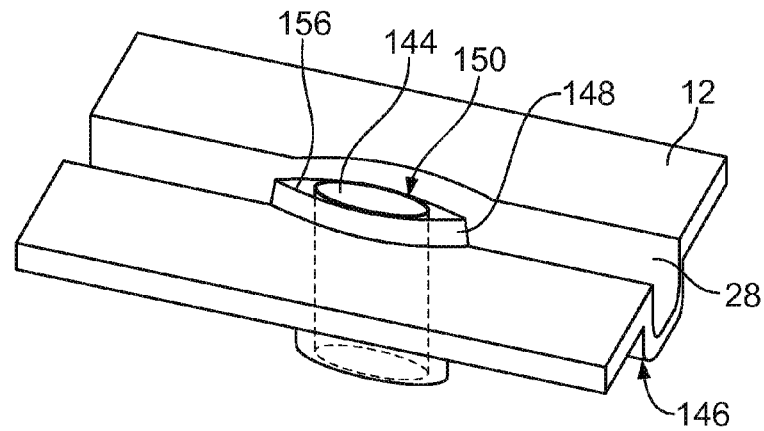
FIG. 16: a perspective view of a fluid guide body having an open main passage and a secondary passage opening therein in accordance with an embodiment of the invention in a sectional representation.

As FIG. 16 shows, and as discussed above, the fluid guide body (i.e., the base body 12) of the cassette 10 has a main fluid passage 28, which is integrally worked into the base body 12 and is closed by a covering film (i.e., the foil 14), which is not shown in FIG. 16.

Figure 17:
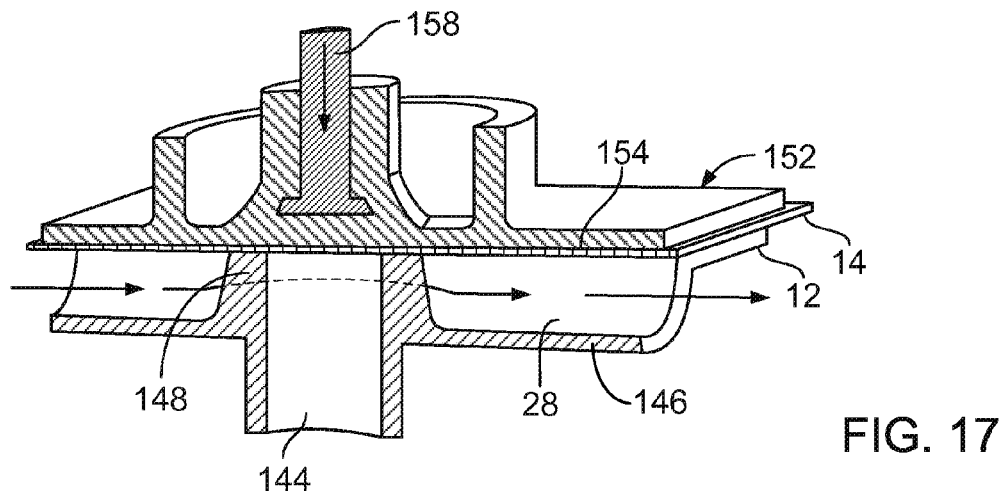
FIG. 17: a perspective view of a base body of the cassette of FIG. 1 in a partial section, wherein a covering film is pressed onto the fluid guide body by a valve actuator and closes the secondary passage.

The fluid guide body (i.e., the base body 12) further has a secondary passage 144 that leads away from the rear side of the base body 12, which is remote from the open side of the main passage 28, onto the opposite front side of the base body 12 and opens there into the main passage 28. As FIG. 17 shows, the secondary passage 144 passes through a base 146 of the main passage 28. The secondary passage 144 extends into the main passage 28 in the form of a volcano-like funnel 148 whose height corresponds to the depth of the main passage 28 so that an orifice 150 of the secondary passage 144 is arranged vertically coincident with the rims of the main passage 28.

The secondary passage 144 is positioned symmetrically in the center of the main passage 28 and extends perpendicularly to the longitudinal direction of the main passage 28. The planar designed orifice 150 is in the plane which is set up by the rims of the main passage 28.

As FIG. 16 shows, the funnel 148 has a streamlined cross-section. In more precise terms, the outside of the wall of the secondary passage 144 in the main passage 28 is formed in streamlined manner, with the longitudinal axis of the streamlined shape corresponding to the longitudinal axis of the main passage 28. Vortexes, turbulences and an increased flow resistance are thereby avoided at the secondary passage 144. The medical fluid flowing through the main passage 28 can flow past the secondary passage 144 in laminar fashion.

As FIG. 16 shows, the contours of the main passage 28 are also formed extending in streamlined fashion around the secondary passage 144. The side walls of the main passage 28 opposite the funnel 148 bulge in streamlined fashion around the funnel 148 so that the fluid flow forking around the funnel 148 finds approximately the same flow cross-section and can flow past the funnel 148 without speed changes.

To be able to close the open side of the secondary passage 144 and simultaneously the orifice 150 of the secondary passage 144, the covering film (i.e., the foil 14), which can be welded or connected in another way to the base body 12, lies on the base body 12. To seal the main passage 28, the foil 14 can be welded to the base body 12 along the rims of the main passage 28. The sealing can, however, also be effected by pressing the foil 14 along the rims of the main passage 28 by a valve plunger 152.

The valve plunger 152 has a continuous, planar plunger surface 154 that is formed by an elastic (e.g., elastomer) machine membrane. Due to the vertically coincident arrangement of the orifice 150 with the rims of the main passage 28, the secondary passage 144 can be closed without stretching of the foil 14, if the foil 14 is pressed onto the base body 12. The orifice 150 is formed for this purpose as a planar valve seat 156, which is in the plane set up by the rims of the main passage 28 and forms the front end of the funnel 148.

FIG. 17 shows the closed state of the secondary passage 144. The plunger surface 154 is pressed onto the base body 12. Additional pressure can be applied by an actuating part 158 in the region of the orifice 150 of the secondary passage 144 in order to achieve a reliable sealing of the secondary passage 144.

Figure 18:
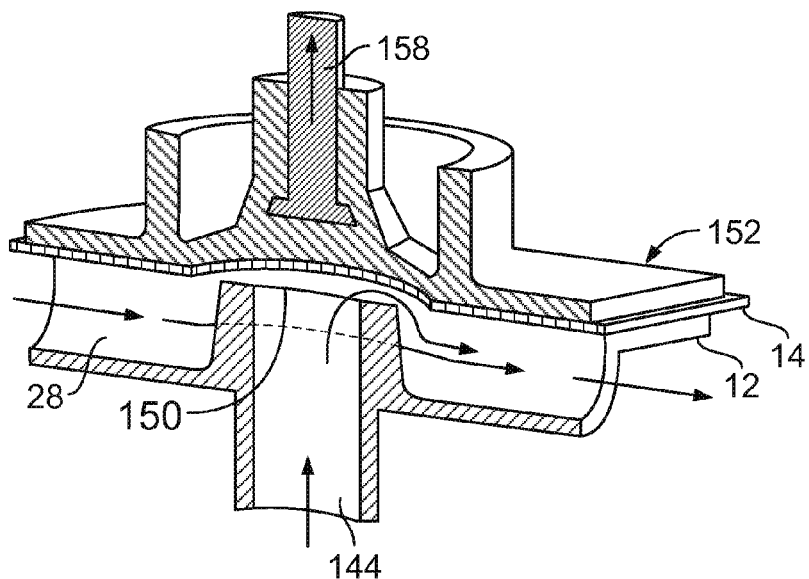
FIG. 18: a perspective view similar to FIG. 17, wherein the secondary passage is represented in its open position.

To open the secondary passage 144, the actuating part 158, which is connected to the plunger surface 154 in the region of the secondary passage orifice 150, is moved away from the base body 12. The plunger surface 154 is thereby raised from the orifice 150 of the secondary passage 144 in the region thereof. As FIG. 18 shows, the plunger surface 154 thereby deforms, which is allowed by the design of the same as an elastic membrane.

The foil 14 also lifts off the orifice 150 of the secondary passage 144 due to the raising of the plunger surface 154. The pressure of the flow in the main passage 28 presses the foil 14 away from the orifice 150. Optionally, this can also be supported actively by the interposition of a vacuum between the plunger surface 154 and the foil 14, which is helpful in particular when a sample should be sucked from the fluid flow in the main passage 28 through the secondary passage 144.

When the actuating part 158 lifts, the foil 14 stretches elastically. The deformation is here very low, however. It is in particular not plastic so that a formation of creases in the subsequent re-closing of the orifice 150 is prevented. As FIG. 18 shows, the secondary passage 144 is in flow communication with the main passage 28 in the raised state of the foil 14.

Other details regarding the phantom valves 46 are described in DE 100 53 441, which is incorporated by reference herein.

Figure 12:
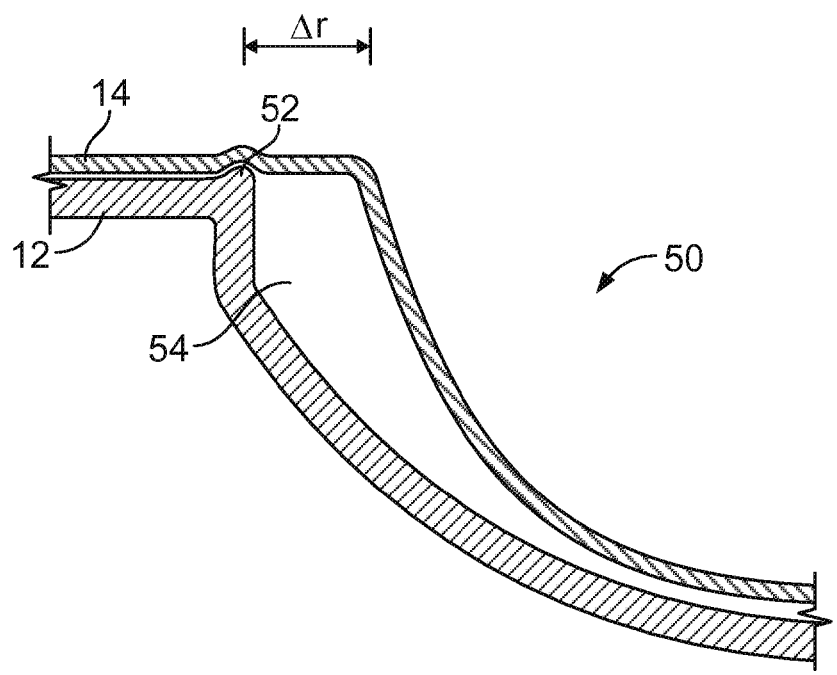
FIG. 12: a partially sectional representation of a pump chamber of the cassette in accordance with the present invention.

Referring again to FIG. 1, reference numbers 50 designate two pump chambers which serve to pump the blood. The design of the pump chambers 50 is shown in detail in FIG. 12. The pump chambers 50, which are activated via membrane pumps provided at the machine side (i.e., in the machine block 108), have substantially tangential inlets and outlets for a uniform throughflow of the total chamber, as shown in FIG. 1. The shape of the pump chambers 50 is pre-determined by the correspondingly shaped base body 12 of the cassette 10 and can be approximately described as a spherical section. At the periphery, the base body 12 of the cassette 10 has a raised edge 52 around the pumping chambers 50 which serves as a stop bead. In addition, as shown in FIG. 12, the peripheral edge of the spherical section is set somewhat lower so that in the pressing-out phase, that is in the phase in which the cover foil 14 is moved toward the base body 12 of the cassette 10, a flushing edge or flushing passage 54 is formed. The flushing edge or flushing passage 54 is advantageously made in that the spherical pump surface at the machine side (i.e., the spherical pump surface in the machine block 108), which is not shown in FIG. 12, has a smaller radius than the radius of the pump chamber 50 at the cassette side. The radius difference $\Delta_r$ is shown in FIG. 12. A wide flushing edge or flushing passage 54 is hereby formed. This flushing edge or flushing passage 54 is an annular space for the pumped blood in the extreme pressing-out position. This free annular space, on the one hand, avoids blood damage by being trapped between the foil surface and the injection molded surface (i.e., the base body 12) at the end of the pressing-out phase and, on the other hand, blood damage due to high flow speeds and shearing strains which would result at the start of the start-up phase if no free annular space were provided.

Figure 10:
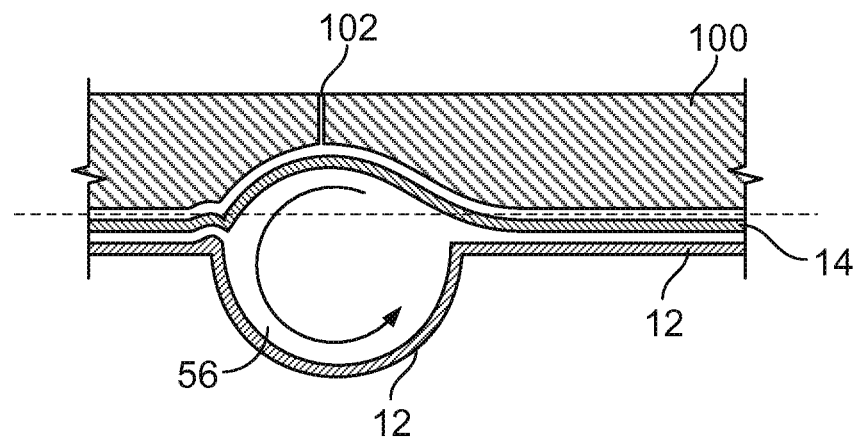
FIG. 10: a detail of a venting unit in the apparatus in accordance with the invention.

In the upper region of the cassette in the installed state, a venting chamber 56 is formed which is shown again in FIG. 10 in a sectional representation. A venting membrane 58 is arranged in this venting chamber via which correspondingly collected air can be separated since it is made as a partially permeable membrane which preferably has hydrophobic or oleophobic properties. Expanded or sintered polytetrafluoroethylene can preferably be used as the venting membrane. A venting stub 60 is arranged above the venting membrane 58 and its cooperation with the fluid treatment machine (not shown in more detail here) will be described later.

Bubbles are trapped in the venting chamber 56 by a slowing down of the blood flow. As shown in FIG. 10, a rotation flow is generated for effective air separation with minimum area requirements on the cassette 10. In this process, the generation of the final rotation flow is only created in the operating state of the cassette 10 in the fluid treatment machine 100. The cover foil 14 of the cassette 10 is pulled into the fluid treatment machine 100 by a corresponding vacuum coupling system of which only one vacuum suction passage 102 is shown in FIG. 10. An almost circular cross-section of the venting chamber 56 is thereby formed. The rotation flow of the blood is supported in that the passage opening into the venting chamber 56 also runs—together with its cover foil 14—slightly into the machine side so that an almost tangential inflow within the chamber is achieved. An effective suction can take place at the machine side at the venting stub 60. A low filling volume results overall here in the venting chamber 56 as a result of the construction.

Figure 13:
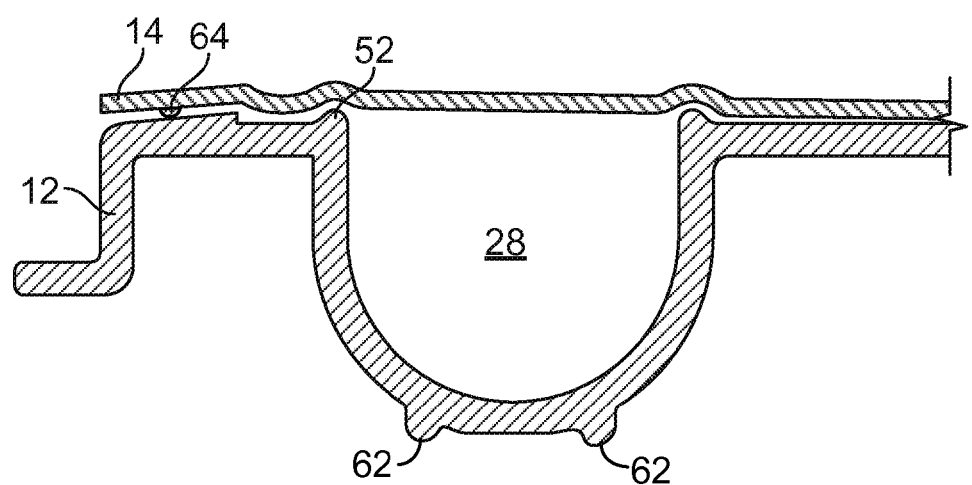
FIG. 13: a partially sectional representation through a passage of the cassette in accordance with an embodiment variant of the invention.

The basic design of the passages 28 can be explained with reference to FIG. 13. Generally, care is taken in the passage design of the passages 28 that a smooth foil surface and smooth passage surfaces are provided. Steps, dead spaces, turbulence and impact surfaces are avoided. Low changes in direction and speed are aimed for. Separations of flow are largely avoided. All passages 28 and also chambers 50 have an edge bead 52 which accompanies the passages and faces the cover foil 14. On insertion of the cassette 10 into the fluid treatment machine 100, the foil 14 is pressed onto the edge bead 52 such that all passages 28 are sealed against the environment. At the rear of the cassette, i.e., at the outer side of the passage wall, webs 62 are formed which accompany the passages and via which the rear pressing force is guided to the edge beads 52 in order thus to achieve a uniform linear distribution of force.

It can also be explained with reference to FIG. 13 that the base body 12 of the cassette 10 is welded to the cover foil 14 at the outer edge 64.

As shown in FIG. 1, the cassette 10 has a recessed centering fork 66 as a positioning aid which receives a centering pin on the machine side on insertion. Stop noses 68 are furthermore molded on which contact against corresponding machine surfaces on insertion. The cassette 10 is thereby guided in height and angle. When pressing the cassette 10 into the fluid treatment machine 100, a latching with the fluid treatment machine takes place at a snap element not shown in more detail here such that the cassette 10 is fixed in an aligned manner. The cassette 10 has a molded handle 70 at the side disposed opposite the centering fork 66 for simplified handling.

The arterial injection septum 16 or the venous injection septum 20 are made in the embodiment shown here, in contrast to a conventional injection position, such that their base body is formed by the base body 12 of the cassette itself so that here only the elastic septum is fixed by a snap ring (not shown in detail here). The septum consists of an elastomer in the embodiment shown here.

Figure 4:
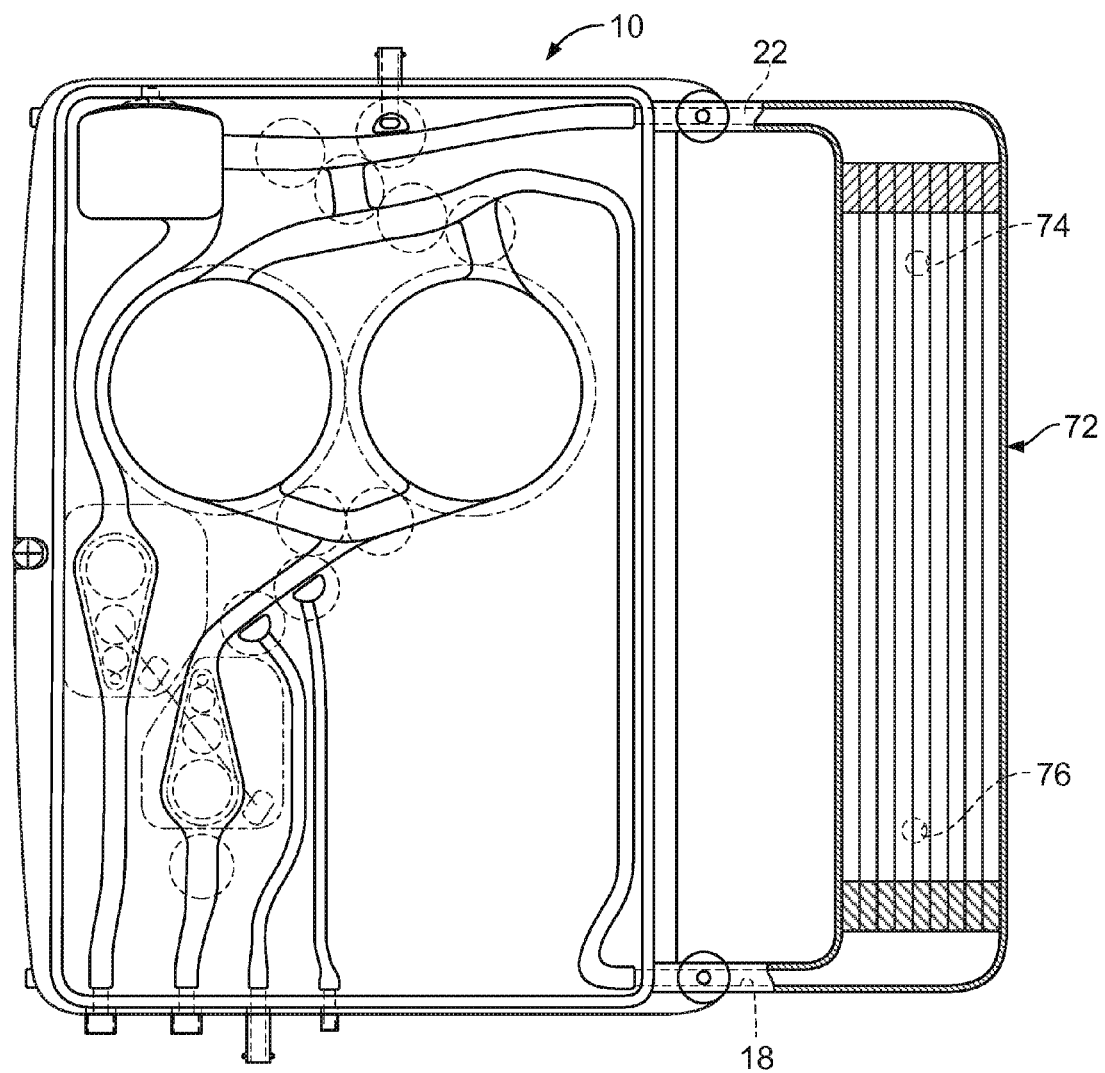
FIG. 4: a schematic plan view of a further aspect of the invention which substantially corresponds to that in accordance with FIG. 1, but has an integrated dialyzer.

FIG. 4 shows a modified embodiment of the cassette in accordance with FIG. 1. This cassette 10 shown in FIG. 4 also serves standard hemodialysis and largely shows an identical design to the cassette 10 in accordance with FIG. 1. To this extent, a detailed description of the already described components of the cassette 10 is superfluous. However, instead of the handle 70 in the embodiment in accordance with FIG. 1, a dialyzer 72 is integrated in the side of the cassette 10, with the lines 18 and 22 to the dialyzer opening directly into the dialyzer. The dialysate connections at the dialyzer, which can have a conventional design, are designated by 74 and 76.

A cassette 10 is shown in FIG. 2 which is designed as an online hemodiafiltration cassette. It becomes clear from the arrangement of the different elements that the base body 12 of the cassette 10 starts from that base body of a cassette such as has already been described in FIG. 1 with reference to the embodiment for standard hemodialysis. All elements which are known from this configuration can be found in the same manner in the embodiment variant in accordance with FIG. 2 for online hemodiafiltration. To this extent, they will not be additionally explained again. However, those parts will be explained which are necessary for the operation of the hemodiafiltration cassette. This includes the substituate connector 80 via which the substituate fluid is fed into the passages 28. Substituate passage valves 82 are provided at the passages and the passages 28 can be closed at the appropriate positions via these valves 82. The substituate fluid is guided into two parallel pump chambers 84, which form substituate pump chambers, via the passages 28. The substituate pump chambers 84 substantially correspond to the pump chambers for the blood 50 as they have previously already been described in detail. Starting from the passage 28, the substituate fluid is guided through a substituate tunnel 86 which is disposed on the opposite side of the base body 12 of the cassette 10. The substituate tunnel 26 is suitably closed at the rear side, e.g., by a welded foil. The substituate fluid 86 can be led into the passage 28 carrying the blood via a port for pre-dilution 88 or via a port for post-dilution 90. The ports are again made as phantom valves of the type described above.

The substituate region substantially formed by the substituate pump chambers 84 is surrounded by a substituate weld rim 92 to which the cover foil 14 is sealingly welded so that this region of the cassette 10 processing substituate is separated from the blood-carrying region.

Figure 5:
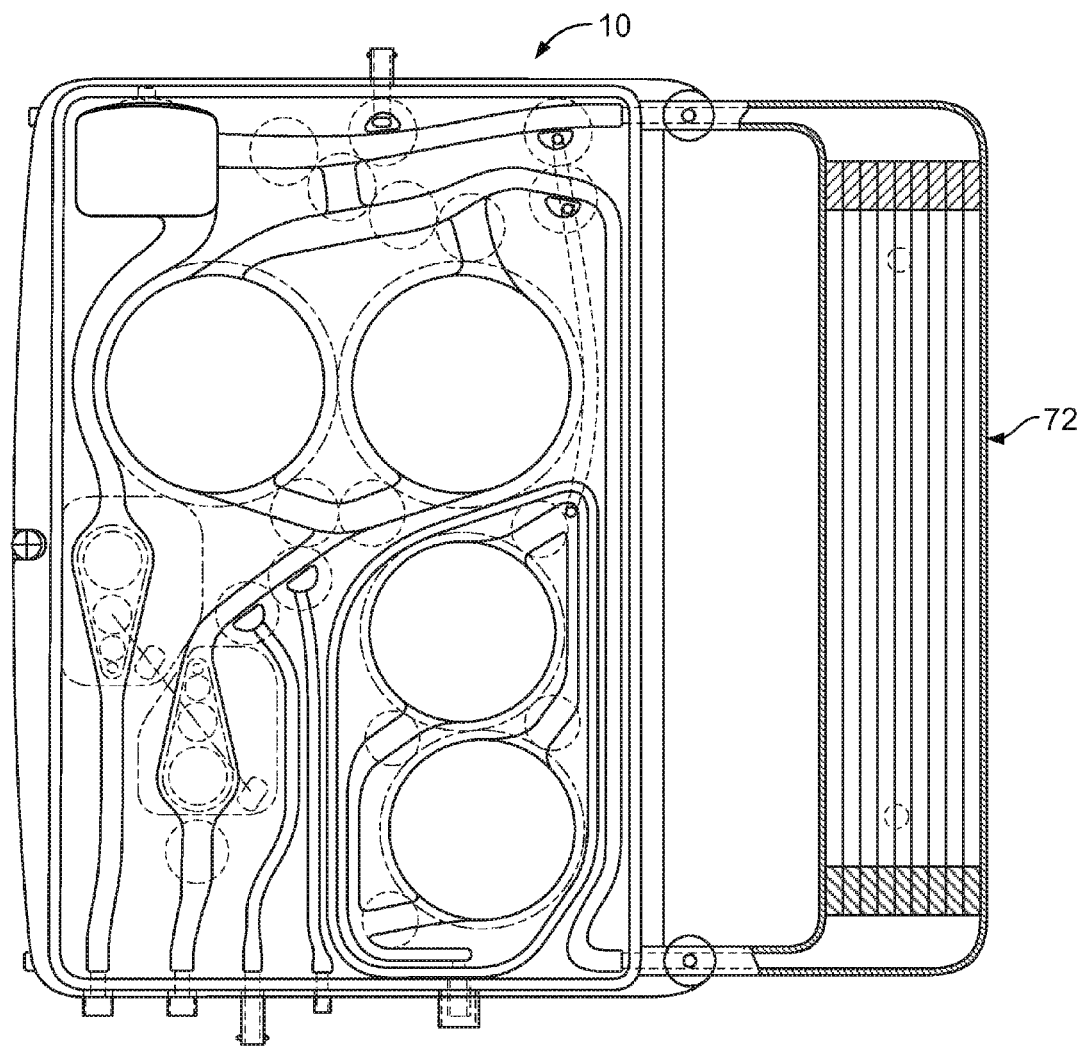
FIG. 5: a further aspect of the invention which substantially corresponds to that in accordance with FIG. 2, but has an integrated dialyzer.

In FIG. 5, a modification of the embodiment variant in accordance with FIG. 2 is shown. Here, too, in a similar manner to the embodiment variant in accordance with FIG. 4, a dialyzer 72 is integrated directly into the cassette 10.

Figure 3:
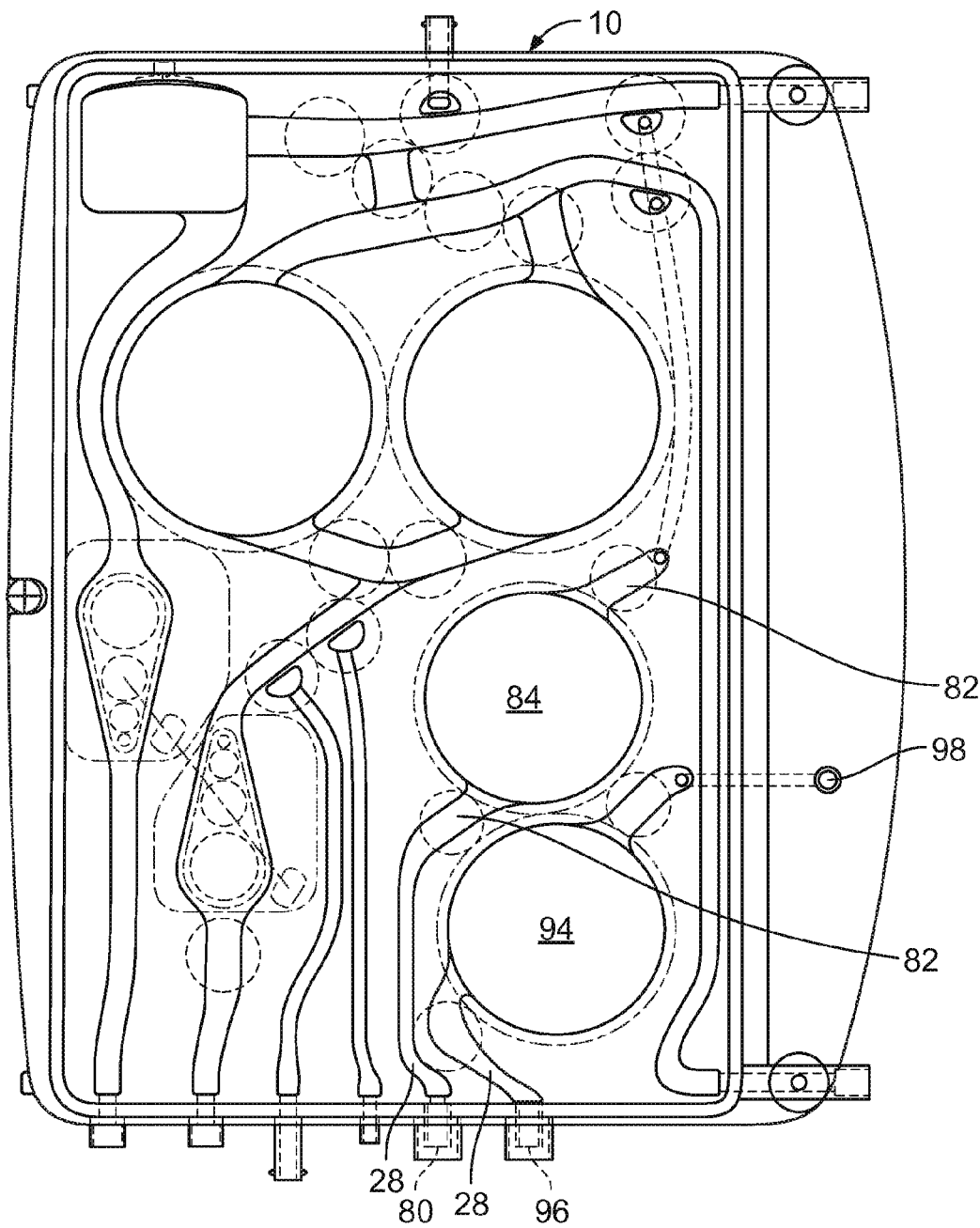
FIG. 3: a plan view of a cassette in accordance with a further embodiment of the present invention which can be used for acute treatment.

In FIG. 3, a cassette 10 for acute treatment is shown as a further integrated embodiment of the cassette. It is designed identically to the embodiment variant in accordance with FIG. 1 in the region of the blood treatment part. With respect to the substituate part, it partly corresponds to the embodiment in accordance with FIG. 2, with here only one substituate pump chamber 84 being provided which is fed by the substituate fluid led in via the substituate connector 80 and the passage 28. In a similar manner as to the embodiment variant in accordance with FIG. 2, substituate passage valves 82 are provided before and after the substituate pump chamber 84. The further pump chamber, which is designated by 94 in the present embodiment variant for acute treatment, is connected to a filtrate outlet 96 via a passage 28 and opens into a filtrate connection 98 which is connected to the dialyzer not shown in any more detail here.

Figure 6:
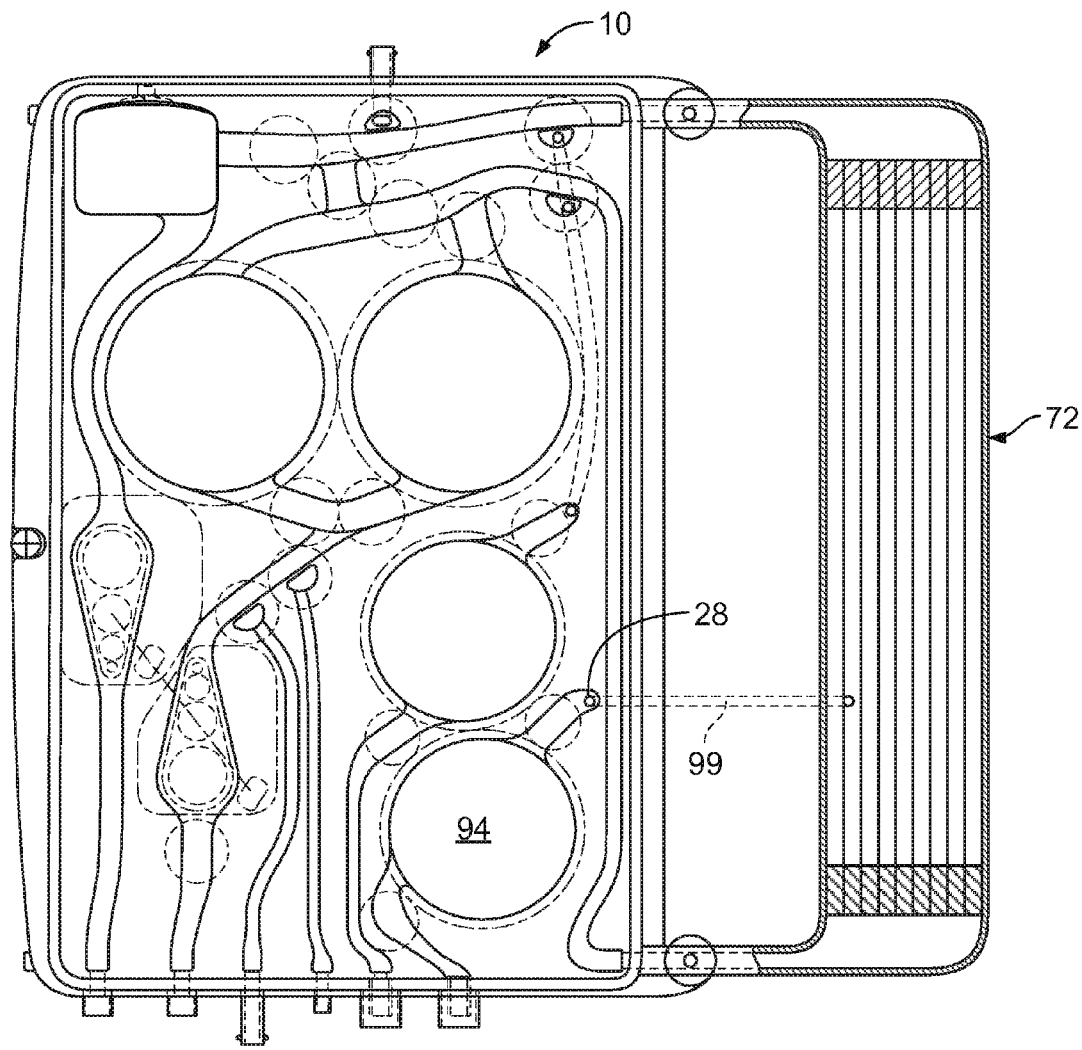
FIG. 6: a further embodiment of the invention which substantially corresponds to that in accordance with FIG. 3, but has an integrated dialyzer.

In FIG. 6, in turn, a modified embodiment variant of the cassette 10 in accordance with FIG. 3 is shown. Here, a dialyzer 72 is in turn integrated instead of the handle, with here a connection 99 being provided between the dialyzer 72 and the passage 28 which carries the filtrate and which leads to the filtrate pump chamber 94.

Figure 7:
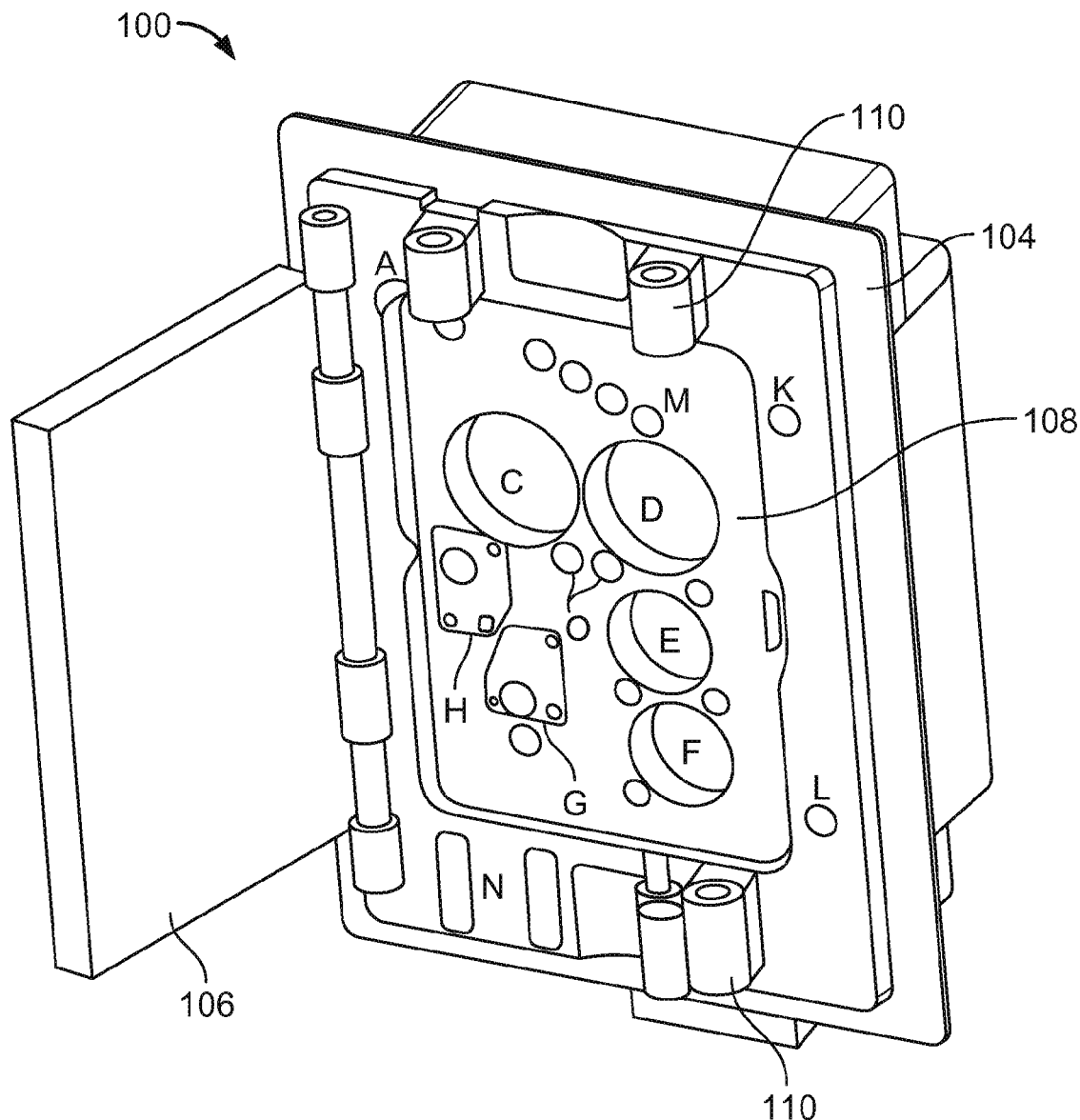
FIG. 7: a three-dimensional representation of a fluid treatment machine as an embodiment of the apparatus in accordance with the invention without an inserted cassette.

In FIG. 7, an embodiment of the fluid treatment machine 100 is shown without an inserted cassette 10. This fluid treatment machine 100 is designed such that all aforesaid cassettes can be inserted, with a basic extracorporeal blood circuit, i.e. a standard dialysis using an external dialyzer, being carried out by a corresponding program selection, for example on insertion of the cassette in accordance with the embodiment variant in accordance with FIG. 1. When a cassette 10 in accordance with the embodiment of FIG. 2 is used, online hemodiafiltration or an online hemofiltration variant is, for example realized by use of the components required for this purpose with, optionally, automatic connections (not shown) to the fluid circuit of the basic unit. Highly integrated variants with an integrated dialyzer and an automatic dialyzer connection are also possible such as are shown by way of the cassette in the embodiment variants in accordance with FIGS. 4 and 5. Acute dialysis treatment is possible when a cassette 10 is used in accordance with the embodiment of FIG. 3.

The fluid treatment machine 100 substantially consists of a frame 104 which surrounds and/or includes or receives the most important components. A door 106 is fitted to the frame 104, on the one hand, and the machine block 108 is guided in the frame, on the other hand. All forces occurring between the door 106 and the interior of the unit are absorbed by means of the frame 104, namely the door hinge, door latch, pressing actuator system and the rear wall. The frame 104 furthermore contains the door latch 110. The cassette 10 is received between the door 106 and the machine block 108, as shown in the FIGS. 8 and 9, and is sealed by pressing. Sensor system elements are included in the cassette region of the machine and they detect whether a cassette is correctly positioned in the fluid treatment machine. These, or further sensor system elements, can be designed such that they are suitable for recognizing the cassette type (e.g. with the aid of a barcode on the cassette).

The important elements for the control and monitoring of the extracorporeal blood circuit, such as pumps, valves, the sensor system, etc., are contained in the machine block 108. This machine block 108 establishes the most important interface to the cassette 10. The cassette surface is coupled to the unit here and the sealing of the cassette 10, and thus the fixing of the flow paths, takes place by this. The machine block 108 is guided movably in the frame and fixes the cassette 10, as already described above, until the door 106 is closed.

Figure 8:
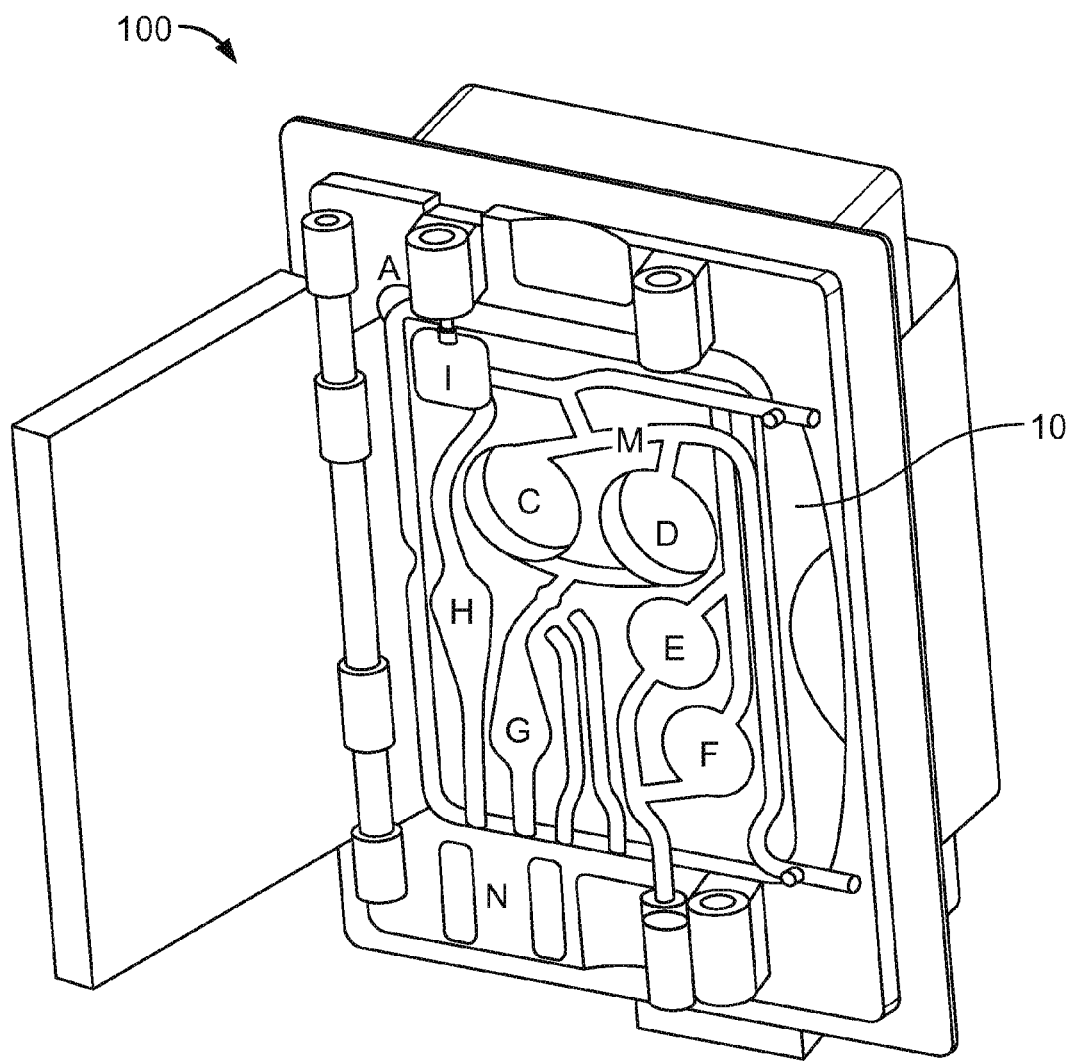
FIG. 8: a representation corresponding to FIG. 7, but with an inserted cassette.
Figure 9:
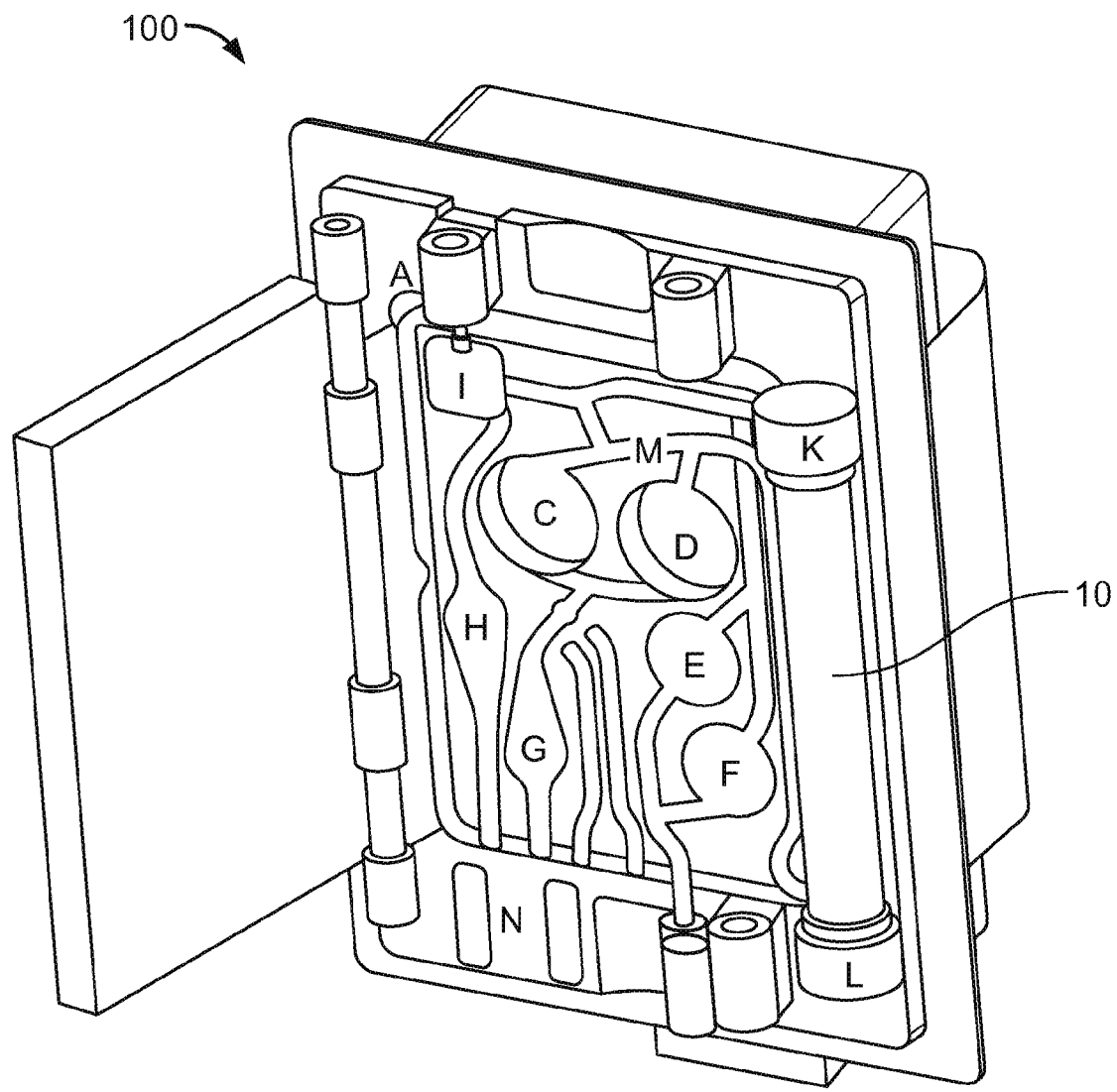
FIG. 9: a representation in accordance with FIG. 7, but with a different embodiment variant of a cassette differing from the cassette shown in FIG. 8.

Hydraulic piston pumps are contained in the fluid treatment machine which are not shown in detail in FIGS. 7, 8 and 9 here. They are, on the one hand, blood pumps or optional substitute feed pumps or ultrafiltrate pumps. They are hydraulically connected to the pump chambers (i.e., the blood pump chambers) C, D, and, in some cases, they are hydraulically connected to the optional filtrate pump chambers and/or the optional substitute pump chambers E, F. Furthermore, compressors for the generation of the required pneumatic pressure (overpressure or vacuum) not shown in more detail here are contained in the fluid treatment machine 100. The fluid treatment machine 100 furthermore has—in a manner not shown in more detail—a pneumatic buffer container for the compensation of pressure fluctuations, a main electronics box, a heparin injection pump and a blood pressure monitor module.

A pressing actuator system on the rear wall of the frame 104, likewise not shown in more detail, must be emphasized here. An inflatable air cushion is integrated here which can move the whole machine block 108, which is movably supported in the frame 104, and press it against the closed door 106.

Furthermore, instead of individual air-carrying tubes, an air distributor plate is provided at the machine block 108 which contains main connections for the pneumatics and which guides compressed air and vacuum to the valves and actuators via passages integrated there without any substantial tubing, with them simultaneously terminating the machine block with respect to the interior of the fluid treatment machine 100.

Optional modules can be provided in the fluid treatment machine 100 for the carrying out of the online hemodiafiltration. For instance, an online feed port for the automatic coupling of a cassette 10 to a dialysate circuit or an online flushing port for the return of flushing solution can be contained here.

The door 106 must be open for the insertion of the cassette 10. The cassette 10 is inserted and, after positioning of the centering fork 66, is fixed to the surface of the machine block by means of a snap hook.

The side of the machine block 108 facing the cassette 10 is lined with a soft elastomer mat 160 (shown in FIG. 19), which seals the cassette 10 after pressing has taken place.

Figure 19:
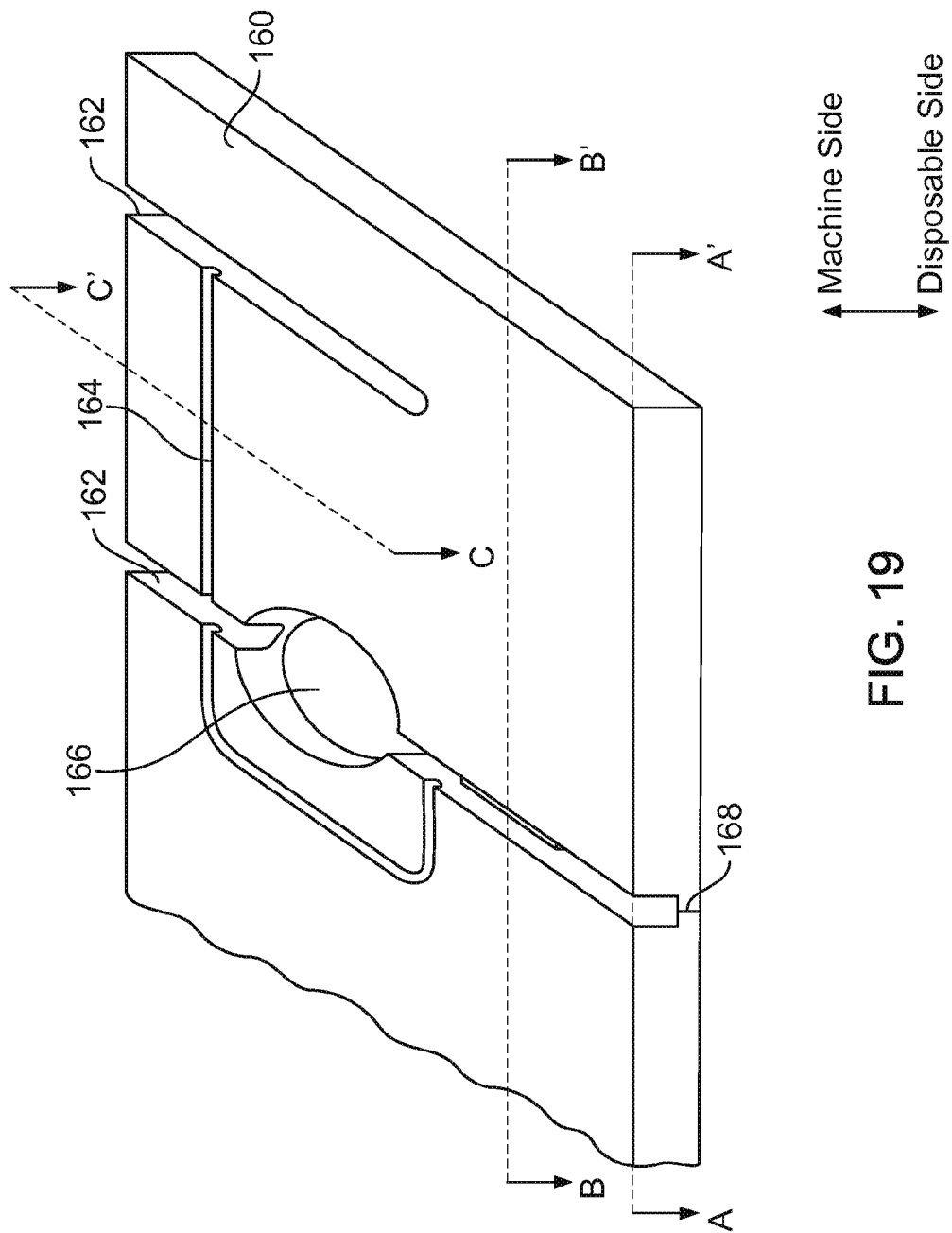
FIG. 19: a schematic, 3D representation of a section of an elastic matt according to an embodiment of the present invention.

Referring to FIG. 19, during use, the elastic matt 160 is arranged between the fluid treatment machine (i.e., the machine block 108), of which no detail is shown here, and the cassette 10. On the so-called machine side, namely on the surface which, when assembled, faces the fluid treatment machine 100, matt channels 162 and connection channels 164 are formed. Furthermore, a recess 166 is arranged in the elastic matt 160, into which in the assembled condition a machine-mounted valve, for example, engages and establishes a seal all around. It is easy to see that this machine-mounted valve interrupts the respective matt channel 162 which happens to join the recess 166. In order to still make an air extraction possible, a connection channel 164 has been provided which connects the two interrupted branches of the matt channel 162 and connects them in turn with a further, parallel matt channel 162. The structure shown here is, of course, only an example and can be changed in any way. While the channel structures are provided on the machine side of the elastic matt 160, the disposable side, namely the side facing the cassette, is executed as a smooth, i.e., flat surface.

Figure 20:
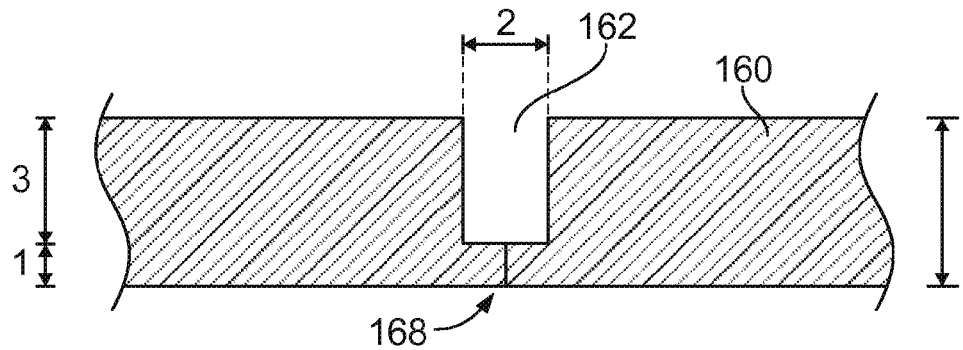
FIG. 20: a section along the section line A-A' in FIG. 19.
Figure 21:
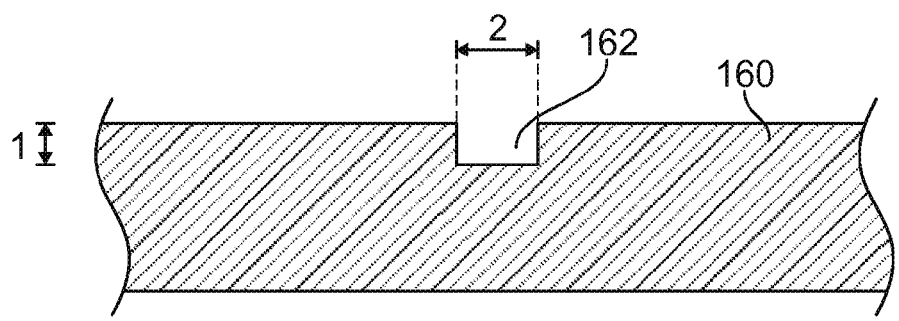
FIG. 21: a section along the section line B-B' in FIG. 19.
Figure 22:
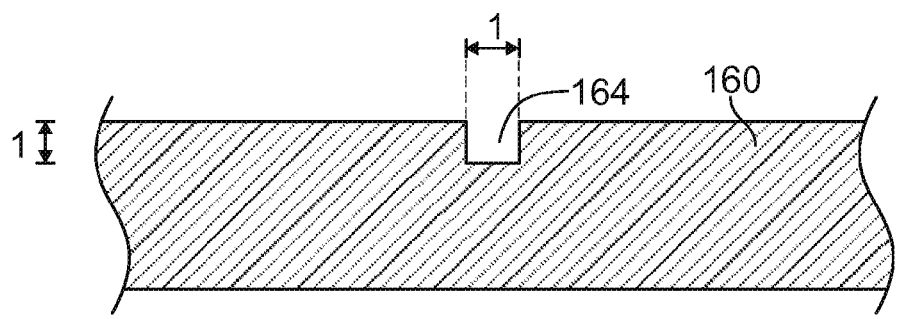
FIG. 22: a section along the section line C-C' in FIG. 19.

By referring to the sectional views of FIGS. 20 to 22, the structure of the individual channels can be explained in more detail. The section A-A' as per FIG. 19 is shown in FIG. 20 where a matt channel 162 becomes visible which, with the elastic matt 160 used here having a thickness of 4 mm, has a depth of 3 mm and a width of 2 mm. In the remaining matt material below the channel 162, which has a thickness of 1 mm, a slit 168 is placed which takes on a type of valve function. When a vacuum is applied, the two areas of the elastic matt 160 adjacent to the slit 168 will open and enable the extraction of air gas. In an idle state or when an equilibrium is obtained, the two adjacent areas return to their original position and close the opening. In order to enhance this return effect, areas between the slits 168 are provided in the matt channel 162, which on the one hand do not have a slit and, on the other hand, are less deeply recessed in the area of matt channel 162. Referring to FIG. 21, a corresponding area can be seen in section B-B', which shows that, while the matt channel 162 in this area has the same width of 2 mm, it only has a depth of 1 mm.

Referring to FIG. 22, a connection channel 164 is shown in the sectional view of C-C', where said channel is narrower and not as deep as the matt channel 162, which can be seen clearly in this view. In this case, both the width of the connection channel 164 and the depth are one millimeter each.

With the elastic matt 160, it is guaranteed that the interior space of the fluid treatment machine, in its idle state, is protected by the self-closing feature of slits 168. At the same time, an even air extraction is achieved between the fluid treatment machine and the cassette across its entire surface because parallel extraction takes place via numerous slits 168. Thus, a minor blockage may not cause any detrimental effects for other areas.

With a thin matt 160, as it has been presented in the embodiment for example, the opening effect of the slits can be utilized by applying a vacuum.

Since the elastic matt 160 is exchangeable, it can be replaced easily after contamination or a fault. It is especially advantageous that no structured shapes are required for the fixed components on the machine. On the side of the elastic matt 160 facing the machine, open structures can be formed so that no sub-surface tunnels or other closed structures are required. On the other hand, the side of the elastic matt 160 facing the cassette is largely formed as a smooth, closed surface which can be cleaned easily for example.

Other details regarding the elastic matt 160 are described in DE 101 57 924.1, which is incorporated by reference herein.

Referring again to FIG. 7, after closing and locking the door 106, pressing takes place by inflating the aforesaid air cushion. On opening and removing the cassette 10, the pressing is cancelled again by letting out the air in the air cushion before opening the door 106.

To achieve a sufficient pressing and to prevent a tilting of the machine block 108 by a non-uniform introduction of force, the air cushion has approximately the size of the machine block 108 or of the cassette 10.

Since, however, further components, for example, control valves or the air distributor plate with the control valves, are now disposed between the air cushion and the machine block, the force transmission takes place by means of spacer bolts.

The traction between the door 106, the frame 104 and the rear wall takes place by the door hinge, the latch 110 and connection bolts, not shown in any more detail here, between the frame and the rear wall.

As already mentioned, a constant pressing of the cassette 10 must take place for a proper operation. For this purpose, it is necessary for the door 106 to be locked during the treatment. This locking takes place via two latching bolts (not shown in any more detail here) at the upper right hand and lower right hand door region, with these moving into two corresponding bores inside the door 106 on actuation, which takes place automatically. The moving in and out takes place pneumatically. An erroneous opening of the door 106 on a failure of the pneumatics is precluded by the bolts moved into the door and by the lateral forces occurring by the pressure load of the door. To check whether the latching has taken place, Hall proximity sensors can be integrated which detect the movement of the bolts. In addition, this signal can be linked to information on the door position which can be picked up by a separate sensor. In addition, the latching bolt not shown in any more detail here can have a latch connection. This latch connection consists of a spring-loaded latch ball on the door side which latches into a corresponding arch of the latch bolt and can hold the door in the corresponding position. An introduction slope is provided for the simplified latching. To open the door from the latch position, the latch ball present here is drawn back by means of a mechanical system.

On the side of the fluid treatment machine 100, the blood circuit substantially consists of at least one hydraulically controlled membrane pump having two independent pump chambers C and D which can be used as a highly precise flow pump or as a volumetric metering unit, a row of valves M, O and clamps N for the control of the flow path, a highly integrated sensor system G, H required for monitoring and control, an active air extractor, i.e., an air separation chamber I with a connected cassette venting A, of the blood circuit (air-free circuit) and a door 106 to fix the cassette 10.

The fluid treatment machine 100 respectively comprises a pneumatic system for the overpressure and a pneumatic system for the underpressure. The underpressure serves, for example, to apply an underpressure between the foil 14 of the cassette 10 and the unit side to prevent a passage restriction on the plastic deformation of the foil, to raise the foil at feed positions and thus to be able to keep the access free, to avoid air compliance in the pump devices and to be able to ensure an air-free coupling between the sensor and the foil at specific sensor positions. The air suction requires openings in the unit side and a suction unit, i.e., a vacuum pump, connected to it, wherein the vacuum distribution should be ensured as uniformly and as reliably as possible over the whole surface. In the idling state, the openings should be at least largely closed to permit a good cleaning here. In operation, however, a problem-free air suction should be possible. This problem is solved by the elastomer mat of the type described above.

In the cassette 10, no passage seals are contained except for the edge region and some safety weld connections. The sealing of all flow paths and passages must therefore take place by pressing. For this purpose, the cassette has sealing beads 52 on the passage rims which have already been described above and which are sealable on the pressing of the disposables between the machine block 108 and the door 106 by pressing into the elastic mat.

The air distributor plate not shown in any more detail here is located on the rear side of the machine block 108 and is connected to the, for example, two membrane pumps of the pneumatic system, namely the overpressure pump and the underpressure pump. The air distributor plate is sealed with respect to the rear side of the machine block by a sealing mat and permits the compressed air and vacuum feed via integrated passage structures so that every valve does not need its own tubing. A plurality of circuits are present on the air distributor plate, namely a vacuum circuit, a compressed air circuit which is directly connected to the compressor for the supply of components which always need compressed air, a compressed air circuit for the protection of sensitive components which may only be charged with compressed air under certain states, with it also being separable from the compressor by an on/off valve and an exhaust circuit.

By integration of a plurality of control valves on the air distributor plate, the electrical supply can also be collected via a small control board. Since a plurality of valves are only needed with specific options, a modular retrofitting capability must be ensured.

The sensor system and the pump connections are guided through the plate through apertures and cut-outs.

Sensors which are collected in integrated sensor modules in the present fluid treatment machine 100 are required for the monitoring and control of the extracorporeal blood circuit. Two respective modules work together as a pair. One module is accommodated in the door 106 and the counter-piece in the machine block 108. Both the arterial branch should be monitored by the arterial measuring chamber G and the venous branch by the venous measuring chamber H. The integrated measurement sensor system is described in detail in the German patent applications DE 198 37 667 A and DE 101 43 137 of the same patent applicant. The sensors together have the following properties or provide the following possibilities:

measurement and monitoring of the blood volume;

measurement of the hematocrit;

measurement and monitoring of the thermal energy balance;

measurement and monitoring of the body temperature;

measurement of the conditions of the fistula (with circulation);

air detection;

fistula pressure measurement.

A multi-sensor module is usually fitted with an ultrasonic sensor for volume monitoring, measurement of the hematocrit and the air detection, with a temperature sensor for the automatic access analysis, body temperature monitoring and thermal energy balance, with a pressure sensor for the pressure monitoring and with an optical sensor for the automatic detection of blood.

The valves M and the pump valves O have a similar design to those valves described above.

In addition to the aforesaid valves which are shown in FIG. 7, so-called phantom valves, which are not drawn in any more detail in this FIG. 7, are additionally present. The design and function of the phantom valves are similar to the design and function of the phantom valves discussed above.

Reference letter N designates safety clamps which serve to achieve a safe state during an alarm in the extracorporeal blood circuit, with them interrupting the patient line and thus any blood flow from or to the patient. To avoid unwanted compliance effects, and since the system is designed for a flow reversal, this safety function must be ensured both on the arterial side and on the venous side so that two blocking clamps N are used which can be mechanically coupled.

The blocking clamps should be effective as close to the patient as possible in order to be able to minimize any interference and to satisfy high safety demands. For this reason, tube clamps are used which act directly on the patient tubes.

A possible embodiment, such as is provided here, consists of the clamping of the tubes against a clamping rail on the inner side of the door by means of a reclosable pneumatically opened clamping slide. Such a system is passively spring-closing, namely without pressure and without current and so is also advantageous in the case of a failure under safety aspects.

In FIG. 8, a fluid treatment machine 100 is shown corresponding to FIG. 7 with an inserted cassette 10 corresponding to FIG. 2. In FIG. 9, in contrast, a fluid treatment machine 100 is shown with a cassette 10 corresponding to the embodiment variant in accordance with FIG. 5, with the dialyzer in the cassette here having an automatic dialysate connection K and L to the fluid treatment machine 100.

The new apparatus shown here follows a strictly modular approach while achieving a high flexibility and deployment possibility also with respect to future deployment possibilities and options. The integrated blood module permits the carrying out of the whole spectrum of the blood treatment procedures, namely standard hemodialysis, online hemodiafiltration and also acute treatment.

It must be pointed out with respect to the acute treatment that the machines serving the acute treatment, i.e., the acute dialysis or acute filtration, have to have a simple design in order to be able to be transported corresponding easily and to be able to work without a complex supply structure (e.g. water connection). In this system, therefore, work is carried out practically without exception with bags with premanufactured solutions. Using the embodiments shown in FIGS. 3 to 6, acute hemofiltration can then be carried out easily in which the substituate is supplied from a bag and filtrate is removed from the filter into an empty bag with the pumps shown. Except for the connection of the bags, no further measure is necessary in this case. It would naturally nevertheless be possible to additionally make a dialysis possible with a corresponding effort. Furthermore, the substituate pump could alternatively be used as a dialysate supply pump if the connections inside the cassette were changed accordingly. Then dialysis fluid filled into bags could be supplied in balanced form to the filter via the membrane pump, while fluid is led out in a controlled manner via the filtrate pump. No further components would also be necessary for the fluid control in such a machine.

Each of these types of treatment can take place both in two-needle and in single-needle mode. Reference is made here to the German patent DE 100 42 324 C1 with respect to the description of the two-needle or single-needle mode.

Other embodiments are within the scope of the following claims.

What is claimed is:

1. A dialysis system, comprising:
a dialysis machine defining a cassette compartment; and
a dialysis fluid cassette configured to be disposed in the cassette compartment, the dialysis fluid cassette comprising
a base defining a recessed region; and
a flexible membrane attached to the base and configured to cooperate with the recessed region to define a first fluid channel when the flexible membrane is pressed against the base,
wherein the base further comprises a member extending into the recessed region, the member defining a second fluid channel that extends to an opening in an end surface of the member, the recessed region and the member being configured such that when the membrane is pressed against the end surface of the member, fluid is permitted to flow around an outer contour of the member in the first fluid channel and through the first fluid channel and fluid is prevented from flowing through the second fluid channel, and when the membrane is spaced from the end surface of the member, fluid is permitted to flow around an outer contour of the member in the first fluid channel and through the first fluid channel and fluid is permitted to flow through the second fluid channel.

2. The dialysis system of claim 1, wherein the base comprises raised rims extending outwardly along edges of the recessed region, the raised rims configured to contact the membrane when the flexible membrane is pressed against the base to define the first fluid channel between the flexible membrane and the recessed region of the base.

3. The dialysis system of claim 2, wherein the end surface of the member is substantially planar with end surfaces of the raised rims.

4. The dialysis system of claim 1, wherein the outer contour of the portion of the member in the recessed region has a streamlined shape corresponding to a flow direction of fluid flow through the first fluid channel.

5. The dialysis system of claim 4, wherein the outer contour of the portion of the member in the recessed region has at least one of an acutely tapering separation edge and a rounded leading edge.

6. The dialysis system of claim 1, wherein the end surface of the member is in the form of a flat valve seat.

7. The dialysis system of claim 1, wherein a longitudinal axis of the second fluid channel extends substantially perpendicularly to a flow direction of the first fluid channel and substantially perpendicular to the flexible membrane.

8. The dialysis system of claim 1, wherein the dialysis machine further comprises a plunger having a first surface configured to press the flexible membrane against portions of the base extending along the edges of the recessed region, and a second surface configured to press the flexible membrane against the end surface of the member, and wherein the first and second surfaces are in the same plane.

9. The dialysis system of claim 8, wherein the first and second surfaces are formed by a common planar plunger surface.

10. The dialysis system of claim 9, wherein the plunger is configured such that the second surface of the plunger can be moved away from the end surface of the member to fluidly connect the first and second fluid channels.

11. A dialysis fluid cassette, comprising:
a base defining a recessed region; and
a flexible membrane attached to the base and configured to cooperate with the recessed region to define a first fluid channel when the flexible membrane is pressed against the base,
wherein the base further comprises a member extending into the recessed region, the member defining a second fluid channel that extends to an opening in an end surface of the member, the recessed region and the member being configured such that when the membrane is pressed against the end surface of the member, fluid is permitted to flow around an outer contour of the member in the first fluid channel and through the first fluid channel and fluid is prevented from flowing through the second fluid channel, and when the membrane is spaced from the end surface of the member, fluid is permitted to flow around an outer contour of the member in the first fluid channel and through the first fluid channel and fluid is permitted to flow through the second fluid channel.

12. The dialysis fluid cassette of claim 11, wherein the base comprises raised rims extending outwardly along edges of the recessed region, the raised rims configured to contact the membrane when the flexible membrane is pressed against the base to define the first fluid channel between the flexible membrane and the recessed region of the base.

13. The dialysis fluid cassette of claim 12, wherein the end surface of the member is substantially planar with end surfaces of the raised rims.

14. The dialysis fluid cassette of claim 11, wherein the outer contour of the portion of the member in the recessed region has a streamlined shape corresponding to a flow direction of fluid flow through the first fluid channel.

15. The dialysis fluid cassette of claim 14, wherein the outer contour of the portion of the member in the recessed region has at least one of an acutely tapering separation edge and a rounded leading edge.

16. The dialysis fluid cassette of claim 11, wherein the end surface of the member is in the form of a flat valve seat.

17. The dialysis fluid cassette of claim 11, wherein a longitudinal axis of the second fluid channel extends substantially perpendicularly to a flow direction of the first fluid channel and substantially perpendicular to the flexible membrane.

18. A dialysis system, comprising:
a dialysis machine defining a cassette compartment; and
a dialysis fluid cassette configured to be disposed in the cassette compartment, the dialysis fluid cassette comprising
a base defining a substantially planar surface and a recessed region extending inwardly from the substantially planar surface; and
a flexible membrane attached to the base and configured to cooperate with the recessed region to define a first fluid channel when the flexible membrane is pressed against the base,
wherein the base further comprises a member extending into the recessed region, the member defining a second fluid channel that extends to an opening in an end surface of the member, and the end surface of the member is substantially planar with surfaces of the base that contact the flexible membrane when the flexible membrane is pressed against the base such that when the flexible membrane is pressed against the end surface of the member, fluid is permitted to flow around the member and through the first fluid channel and fluid is prevented from flowing through the second fluid channel, and when the flexible membrane is spaced from the end surface of the member, fluid is permitted to flow around the member and through the first fluid channel and fluid is permitted to flow through the second fluid channel.

19. The dialysis system of claim 18, wherein the base comprises raised rims extending outwardly from the substantially planar surface along edges of the recessed region, the raised rims configured to contact the membrane when the flexible membrane is pressed against the base to define the first fluid channel between the flexible membrane and the recessed region of the base.

20. The dialysis system of claim 19, wherein the end surface of the member is substantially planar with end surfaces of the raised rims.

21. The dialysis system of claim 18, wherein the flexible membrane is configured to close the opening in the end surface of the member when the flexible membrane is pressed against the end surface of the member.

22. The dialysis system of claim 18, wherein an outer contour of the portion of the member in the recessed region has a streamlined shape corresponding to a flow direction of fluid flow through the first fluid channel.

23. The dialysis system of claim 22, wherein the outer contour of the portion of the member in the recessed region has at least one of an acutely tapering separation edge and a rounded leading edge.

24. The dialysis system of claim 18, wherein the end surface of the member is in the form of a flat valve seat.

25. The dialysis system of claim 18, wherein a longitudinal axis of the second fluid channel extends substantially perpendicularly to a flow direction of the first fluid channel and substantially perpendicular to the flexible membrane.

26. The dialysis system of claim 18, wherein the dialysis machine further comprises a plunger having a first surface configured to press the flexible membrane against portions of the base extending along the edges of the recessed region, and a second surface configured to press the flexible membrane against the end surface of the member, and wherein the first and second surfaces are in the same plane.

27. The dialysis system of claim 26, wherein the first and second surfaces are formed by a common planar plunger surface.

28. The dialysis system of claim 27, wherein the plunger is configured such that the second surface of the plunger can be moved away from the end surface of the member to fluidly connect the first and second fluid channels.

29. The dialysis system of claim 28, wherein the flexible membrane is configured so that fluid pressure within the first fluid channel forces the flexible membrane away from the end surface of the member when the second surface of the plunger is moved away from the end surface of the member.

30. A dialysis fluid cassette, comprising:
a base defining a substantially planar surface and a recessed region extending inwardly from the substantially planar surface; and
a flexible membrane attached to the base and configured to cooperate with the recessed region to define a first fluid channel when the flexible membrane is pressed against the base,
wherein the base further comprises a member extending into the recessed region, the member defining a second fluid channel that extends to an opening in an end surface of the member, and the end surface of the member is substantially planar with surfaces of the base that contact the flexible membrane when the flexible membrane is pressed against the base such that when the flexible membrane is pressed against the end surface of the member, fluid is permitted to flow around the member and through the first fluid channel and fluid is prevented from flowing through the second fluid channel, and when the flexible membrane is spaced from the end surface of the member, fluid is permitted to flow around the member and through the first fluid channel and fluid is permitted to flow through the second fluid channel.

31. The dialysis fluid cassette of claim 30, wherein the base comprises raised rims extending outwardly from the substantially planar surface along edges of the recessed region, the raised rims configured to contact the membrane when the flexible membrane is pressed against the base to define the first fluid channel between the flexible membrane and the recessed region of the base.

32. The dialysis fluid cassette of claim 31, wherein the end surface of the member is substantially planar with end surfaces of the raised rims.

33. The dialysis fluid cassette of claim 30, wherein the flexible membrane is configured to close the opening in the end surface of the member when the flexible membrane is pressed against the end surface of the member.

34. The dialysis fluid cassette of claim 30, wherein an outer contour of the portion of the member in the recessed region has a streamlined shape corresponding to a flow direction of fluid flow through the first fluid channel.

35. The dialysis fluid cassette of claim 34, wherein the outer contour of the portion of the member in the recessed region has at least one of an acutely tapering separation edge and a rounded leading edge.

36. The dialysis fluid cassette of claim 30, wherein the end surface of the member is in the form of a flat valve seat.

37. The dialysis fluid cassette of claim 30, wherein a longitudinal axis of the second fluid channel extends substantially perpendicularly to a flow direction of the first fluid channel and substantially perpendicular to the flexible membrane.

* * * * *